(12) United States Patent
Greaves et al.

(10) Patent No.: US 7,235,645 B2
(45) Date of Patent: Jun. 26, 2007

(54) CATIONIC AZO MONOMERS OR SYMMETRIC DIMERS, PREPARATION THEREOF, COMPOSITIONS COMPRISING SAME AND PROCESS FOR DYEING KERATIN FIBERS

(75) Inventors: Andrew Greaves, Montevrain (FR); Bérangère Baril, Suresnes (FR)

(73) Assignee: L'Oreal, S.A., Paris (FR)

(*) Notice: Subject to any disclaimer, the term of this patent is extended or adjusted under 35 U.S.C. 154(b) by 42 days.

(21) Appl. No.: 11/187,812

(22) Filed: Jul. 25, 2005

(65) Prior Publication Data

US 2006/0037152 A1 Feb. 23, 2006

Related U.S. Application Data

(60) Provisional application No. 60/591,931, filed on Jul. 29, 2004.

(51) Int. Cl.
C09B 44/06 (2006.01)
A61Q 5/10 (2006.01)
(52) U.S. Cl. .................... 534/603; 534/604; 8/405; 8/406; 8/407; 8/426
(58) Field of Classification Search ................ 534/603, 534/604; 8/405, 407, 426, 406
See application file for complete search history.

(56) References Cited

U.S. PATENT DOCUMENTS 3,524,842 A * 8/1970 Grossmann et al. ........ 534/613
4,823,985 A 4/1989 Grollier et al.
6,432,146 B1 8/2002 Rondeau

FOREIGN PATENT DOCUMENTS

| EP | 0 630 946 A1 | 12/1994 |
|---|---|---|
| EP | 0 668 327 A1 | 8/1995 |
| FR | 1 533 643 | 7/1968 |
| FR | 2 096 377 | 2/1972 |
| FR | 2 586 913 | 3/1987 |
| GB | 1 195 386 | 6/1970 |

OTHER PUBLICATIONS

French Search Report for FR 04 08186, dated Mar. 24, 2005, Examiner S. Fanni.

English language Derwent Abstract of EP 0 630 946 A1, Dec. 28, 1994.
English language Derwent Abstract of EP 0 668 327 A1, Aug. 23, 1995.
English language Derwent Abstract of FR 2 096 377, Feb. 18, 1972.

* cited by examiner

*Primary Examiner*—Fiona T. Powers
(74) *Attorney, Agent, or Firm*—Finnegan, Henderson, Farabow, Garrett & Dunner LLP

(57) ABSTRACT

Disclosed herein are compounds of formulae (I) and (II) below, and also to processes for the synthesis thereof:

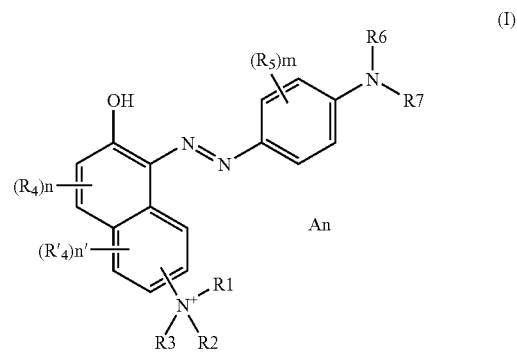

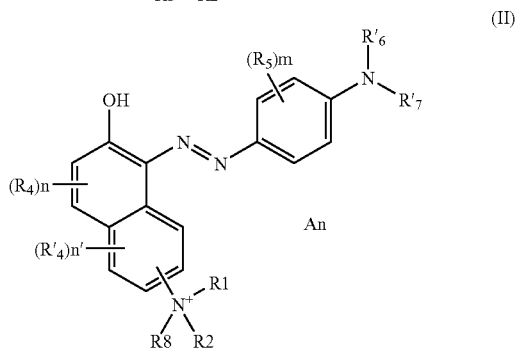

Also disclosed herein are dye compositions comprising said compounds, as cationic direct dyes, and methods for dyeing keratin fibers, for example, human keratin fibers, using these compositions.

40 Claims, No Drawings

CATIONIC AZO MONOMERS OR SYMMETRIC DIMERS, PREPARATION THEREOF, COMPOSITIONS COMPRISING SAME AND PROCESS FOR DYEING KERATIN FIBERS

This application claims benefit of U.S. Provisional Application No. 60/591,931, filed Jul. 29, 2004, the contents of which are incorporated herein by reference. This application also claims benefit of priority under 35 U.S.C. § 119 to French Patent Application No. 04 08186, filed Jul. 23, 2004, the contents of which are also incorporated by reference.

Disclosed herein are cationic azo compounds and their addition salts, in the form of a monomer or a symmetric dimer, and processes for preparing them. Also disclosed herein are dye compositions comprising said cationic azo compounds, as cationic direct dyes, and also methods for dyeing keratin fibers, for example, human keratin fibers, using these compositions.

The field of the present invention relates to the dyeing of keratin materials, for example, human keratin materials, and more particularly to the dyeing of human keratin fibers, such as the hair.

It is a common activity to change the color of hair, whether or not the latter are pigmented, and in most cases, the desired color remains within natural shades.

Several types of dyeing exist, among which are permanent dyeing (also called oxidation dyeing) and direct dyeing (also called semi-permanent dyeing), with or without a lightening effect on the fibers.

In the field of oxidation dyeing, the compounds used are oxidation dye precursors, more particularly oxidation bases optionally combined with at least one coupler. These compounds are substances with little or no color, which, by means of an oxidative condensation process, in the presence of an oxidizing agent, produce compounds which dye the fibers.

In the field of semi-permanent dyeing, the composition applied to the fibers generally comprises at least direct dyes, which are coloring and colored compounds and may optionally also comprise at least one oxidizing agent if it is desired to obtain a lightening effect combined with the coloration.

One of the main difficulties encountered lies in the fact that, in order to achieve such colorations, it is necessary to use precise mixtures of dyes, both in terms of the nature of the dyes and in terms of their respective proportions.

While the result immediately after dyeing may be satisfactory, problems in terms of the coloration changing over time may, however, be encountered. This is because the dyes used in the mixture do not all have the same affinity for the fiber, these differences possibly being further accentuated by the state of sensitization of the fibers. They neither have the same resistance with respect to outside factors, for example, ultraviolet rays, nor the same resistance with respect to the treatments used on the fibres, for instance, shampoos. This often results in a more or less pronounced changing of the color due to the departure of at least one of the dyes present.

Direct dyes exist that make it possible, by themselves, to obtain natural colorations. Among these direct dyes, mention may in particular be made of the Basic Brown 16 dye (Color Index 12250) and Basic Brown 17 dye (Color Index 12251). However, these dyes only moderately withstand shampoo.

Therefore, disclosed herein are compounds which may be useful as direct dyes for dyeing human keratin materials, in particular fibers, which make it possible to obtain natural colorations, for example browns, without it being necessary to use mixtures of various dyes, and the fastness of which may be improved compared with the Basic Brown 16 and 17 dyes mentioned above.

Disclosed herein are compounds of formulae (I) and (II) below, and the addition salts thereof:

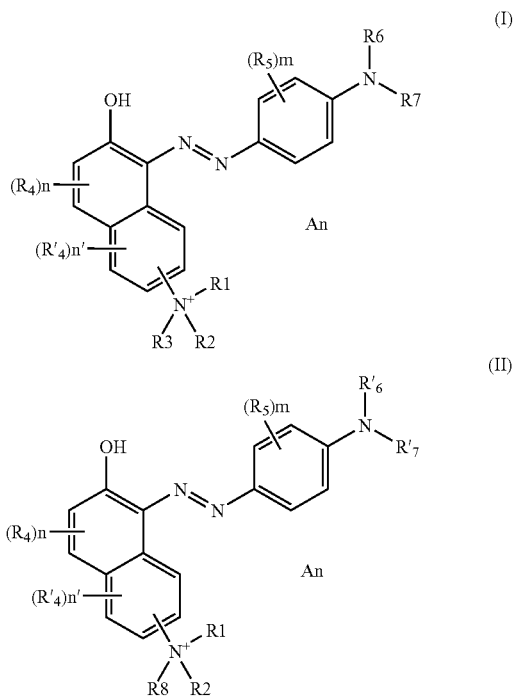

in which:

R1, R2, and R3, which may be identical or different, are chosen from:

linear or branched $C_1$–$C_4$ alkyl radicals that are unsubstituted or substituted with at least one entity chosen from:
  hydroxyl groups;
  linear or branched $C_1$–$C_4$ alkoxy groups;
  amino groups; and
  amino groups substituted with one or two radicals chosen from linear or branched $C_1$–$C_4$ alkyl radicals and linear or branched $C_1$–$C_4$ hydroxyalkyl radicals, which may be identical or different, wherein two of the radicals R1, R2, and R3 may optionally form a saturated or unsaturated, 5- or 6-membered heterocycle optionally comprising another hetero atom chosen from oxygen and nitrogen, said heterocycle being optionally substituted;

R4, R'4, and R5, which may be identical or different, are chosen from:

halogen atoms, for example, chlorine and fluorine;

hydroxyl groups;

nitro groups;

cyano groups;

linear or branched $C_1$–$C_4$ alkyl radicals, optionally comprising at least one entity chosen from hydroxyl groups, linear or branched $C_1$–$C_4$ alkoxy groups, amino groups, and amino groups substituted with one or two radicals chosen from linear or branched $C_1$–$C_4$ alkyl radicals, which may be identical or different;

linear and branched $C_1$–$C_4$ alkoxy radicals;

amino radicals;

amino radicals substituted with one or two radicals, which may be identical or different, chosen from linear or branched $C_1$–$C_4$ alkyl radicals optionally substituted with at least one radical chosen from:

hydroxyl groups;

amino groups;

amino groups substituted with one or two radicals chosen from linear or branched $C_1$–$C_4$ alkyl radicals and linear or branched $C_1$–$C_4$ hydroxyalkyl radicals, which may be identical or different;

substituted amino groups in which the radicals form a saturated or unsaturated 5- or 6-membered heterocycle optionally comprising another hetero atom chosen from oxygen and nitrogen; said heterocycle being optionally substituted;

—$SO_2NHR$ groups, in which R is chosen from hydrogen and $C_1$–$C_4$ alkyl radicals, optionally substituted with at least one radical chosen from hydroxyl radicals, amino radicals, and amino radicals substituted with one or two radicals chosen from linear or branched $C_1$–$C_4$ alkyl and linear or branched $C_1$–$C_4$ hydroxyalkyl radicals, which may be identical or different, wherein two radicals R5 carried by two adjacent carbon atoms may also form, with the carbon atom to which each is attached, an optionally substituted 6-membered aromatic ring;

R6, R'6 and R'7, which may be identical or different, are chosen from:

hydrogen;

linear or branched $C_1$–$C_8$ alkyl radicals that are unsubstituted or substituted with an entity chosen from hydroxyl groups, linear or branched $C_1$–$C_4$ alkoxy groups, amino groups, and amino groups substituted with one or two radicals chosen from linear or branched $C_1$–$C_4$ alkyl and linear or branched $C_1$–$C_4$ hydroxyalkyl radicals, which may be identical or different; possibly interrupted with an entity chosen from hetero atoms chosen from oxygen and nitrogen and groups comprising a hetero atom, such as CO and $SO_2$;

wherein the radicals R'6 and R'7 may optionally form a saturated or unsaturated 5- or 6-membered heterocycle optionally comprising another hetero atom chosen from oxygen and nitrogen; said heterocycle being optionally substituted;

R7 is chosen from groups represented by formulae (a) and (b):

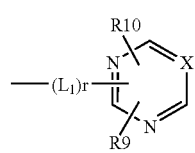

(a)

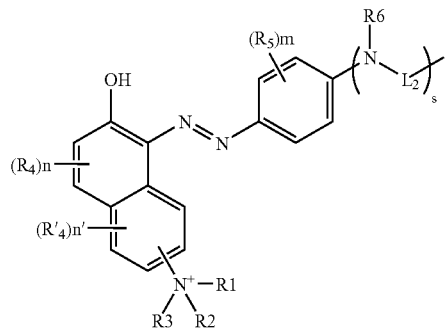

(b)

R8 is chosen from groups represented by formula (c):

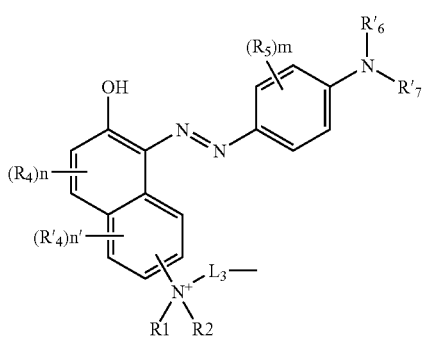

(c)

wherein R1, R2, R3, R4, R'4, R5, R6, R'6 and R'7, in formulae (a), (b), and (c), have the same meaning as above;

R9 and R10, which may be identical or different, are chosen from:

hydrogen, halogen atoms, for example, chlorine and fluorine, nitro groups, cyano groups, linear or branched $C_1$–$C_4$ alkyl radicals optionally carrying at least one entity chosen from hydroxyl groups, linear or branched $C_1$–$C_4$ alkoxy groups, amino groups, and amino group substituted with one or two radicals chosen from linear or branched $C_1$–$C_4$ alkyl radicals, which may be identical or different, hydroxyl groups, linear or branched $C_1$–$C_4$ alkoxy radicals, amino radicals, amino radicals substituted with one or two radicals, which may be identical or different, chosen from linear or branched $C_1$–$C_6$ alkyl radicals optionally substituted with at least one radical chosen from amino radicals, hydroxyl radicals, ammonium radicals, ($C_1$–$C_4$)alkylammonium radicals, imidazolium radicals, pyrazolium radicals, pyridinium radicals, and amino radicals substituted with one or two radicals chosen from linear or branched $C_1$–$C_4$ alkyl and linear or branched $C_1$–$C_4$ alkoxy radicals, which may be identical or different, substituted amino radicals in which the radicals form a saturated or unsaturated 5- or 6-membered heterocycle optionally comprising another hetero atom chosen from oxygen and nitrogen; said heterocycle being optionally substituted;

with the proviso that R9 and R10, which may be identical or different, may not simultaneously represent chlorine or fluorine;

X is chosen from nitrogen and the group —CR11, wherein R11 is chosen from:
hydrogen,
halogen atoms, for example, chlorine and fluorine,
nitro groups;
cyano groups,
linear or branched $C_1$–$C_4$ alkyl radicals optionally comprising at least one group chosen from hydroxyl groups, linear or branched $C_1$–$C_4$ alkoxy groups, amino groups, and amino groups substituted with one or two radicals chosen from linear or branched $C_1$–$C_4$ alkyl radicals, which may be identical or different,
linear or branched $C_1$–$C_4$ alkoxy radicals,
amino radicals,
hydroxyl groups,
amino radicals substituted with one or two radicals, which may be identical or different, chosen from linear or branched $C_1$–$C_6$ alkyl radicals optionally substituted with at least one radical chosen from amino radicals, hydroxyl radicals, and amino radicals substituted with one or two radicals chosen from linear or branched $C_1$–$C_4$ alkyl radicals and linear or branched $C_1$–$C_4$ hydroxyalkyl radicals, which may be identical or different,
substituted amino radicals in which the radicals form a saturated or unsaturated 5- or 6-membered heterocycle optionally comprising another hetero atom chosen from oxygen or nitrogen; said heterocycle being optionally substituted;
L1, which may be cationic or noncationic, is chosen from linear, branched, or cyclic, saturated or unsaturated $C_2$–$C_{20}$ hydrocarbon-based chains, optionally interrupted or terminated by a group comprising at least one hetero atom, optionally interrupted by at least one aromatic or nonaromatic, substituted or unsubstituted heterocycle or ring;
L2, which may be cationic or noncationic, is chosen from:
saturated or unsaturated, linear, branched or cyclic $C_1$–$C_{20}$ hydrocarbon-based chains optionally interrupted or terminated by a group comprising at least one hetero atom, optionally interrupted or terminated by at least one optionally substituted, aromatic, or nonaromatic heterocycle or ring;
aromatic or nonaromatic (hetero)cyclic radicals optionally attached to the nitrogen atoms by means of a group comprising at least one hetero atom, for example, CO and $SO_2$ groups;
L3, which may be cationic or noncationic, is chosen from linear, branched, or cyclic, saturated or unsaturated $C_2$–$C_{20}$ hydrocarbon-based chains optionally interrupted or terminated by a group comprising at least one hetero atom, optionally interrupted by at least one optionally substituted aromatic or nonaromatic heterocycle or ring;
n is a coefficient less than or equal to 2;
n' is a coefficient less than or equal to 3;
m is a coefficient less than or equal to 4;
r is a coefficient equal to 0 or 1;
s is a coefficient equal to 0 or 1; and
An is at least one cosmetically acceptable counterion for ensuring the electroneutrality of the compounds of formulae (I) and (II) or the addition salts thereof.

Also disclosed herein are processes for synthesizing such compounds.

Further disclosed herein are dye compositions comprising, in a cosmetically acceptable medium, at least one compound of formula (I) or (II), and the addition salts thereof, as a direct dye; and a process for dyeing keratin fibers in which an above-mentioned dye composition is applied to dry or wet fibers, with or without final rinsing.

Other characteristics and advantages of the present invention will emerge more clearly on reading the description and examples which follow.

As used herein, and unless otherwise indicated, the limits delimiting a range of values are understood to be part of that range.

In addition, the dimers of formula (I) in which R7 is represented by formula (b) are referred to as 'symmetric' in the following cases:

With s equal to 1, when the radicals R1, R2, R3, R4, R'4, R5, and R6 of formula (I), which may be identical or different, and the radicals R1, R2, R3, R4, R'4, R5, and R6, which may be identical or different, of formula (b), are the same and are placed in the same positions, in formula (I) and in formula (b).

With s equal to 0, when the radicals R1, R2, R3, R4, R'4, and R5, of formula (I), which may be identical or different, and the radicals R1, R2, R3, R4, R'4, and R5, which may be identical or different, of formula (b), are the same and are placed in the same positions, in formula (I) and in formula (b).

The dimers of formula (II) with R8 represented by formula (c) are referred to as 'symmetric' when the radicals R1, R2, R4, R'4, R5, R'6, and R'7, which may be identical or different, of formula (II), and the radicals R1, R2, R4, R'4, R5, R'6, and R'7, which may be identical or different, of formula (c), are the same and are placed in the same positions, in formula (II) and in formula (c).

In other words, the radicals R1 of formula (I), R2 of formula (I), R3 of formula (I), R4 of formula (I), etc., are respectively the same as the radicals R1 of formula (II), R2 of formula (II), R3 of formula (II), R4 of formula (II), etc. In addition, these radicals are located, respectively, in the same position from one ring to the other; the values of the coefficients n, n' and m, respectively, being identical from one formula to the other.

In addition, in formulae (I), (II), (b) and (c), when the coefficients n, n' and m that define the number of substituents carried by the aromatic rings do not take their maximum value, then the unsubstituted carbon atom carries a hydrogen atom.

As used herein, and unless otherwise indicated, a cyclic or heterocyclic radical is referred to as 'substituted' when it carries at least one radical chosen from:
hydroxyl groups,
linear or branched $C_1$–$C_4$ alkyl groups,
linear or branched $C_1$–$C_4$ hydroxyalkyl groups,
linear or branched $C_1$–$C_4$ alkoxy groups,
linear or branched $C_1$–$C_4$ alkylamide groups,
amino groups,
amino groups substituted with one or two radicals chosen from linear or branched $C_1$–$C_4$ alkyl radicals and linear or branched $C_1$–$C_4$ alkoxy radicals, which may be identical or different,
ammonium, $(C_1$–$C_4)$alkylammonium, imidazolium, pyrazolium, and pyridinium groups, and
—$SO_2NHR$ groups and —$NHRSO_2R'$ groups, wherein R is chosen from hydrogen, linear or branched $C_1$–$C_4$ alkyl radicals optionally substituted with at least one radical chosen from hydroxyl radicals, amino radicals, and amino radicals substituted with one or two radicals chosen from linear or branched $C_1$–$C_4$ alkyl radicals and linear or branched $C_1$–$C_4$ hydroxyalkyl radicals, which may be identical or different, and R' is chosen from optionally substituted, linear or branched $C_1$–$C_4$ alkyl radicals.

As indicated above, one embodiment of the present disclosure relates to compounds of formulae (I) and (II) detailed above.

In another embodiment, in formulae (I) and (II), the radicals R1, R2 and R3, which may be identical or different, are chosen from linear or branched $C_1$–$C_4$ alkyl radicals that are unsubstituted or substituted with at least one hydroxyl group; linear or branched $C_1$–$C_4$ alkoxy radicals; amino radicals, and amino radicals substituted with one or two radicals chosen from linear or branched $C_1$–$C_4$ alkyl radicals and linear or branched $C_1$–$C_4$ hydroxyalkyl radicals, which may be identical or different.

In a further embodiment, the radicals R1, R2 and R3, which may be identical or different, are chosen from linear $C_1$–$C_4$ alkyl radicals that are unsubstituted or substituted with at least one hydroxyl group.

Radicals R4, R'4, and R5, of formulae (I) and (II), which may be identical or different, may be chosen from:
 halogen atoms, for example, chlorine,
 hydroxyl groups,
 nitro groups,
 linear or branched $C_1$–$C_4$ alkyl radicals optionally substituted with at least one entity chosen from hydroxyl groups and linear or branched $C_1$–$C_4$ alkoxy groups,
 linear and branched $C_1$–$C_4$ alkoxy radicals,
 amino radicals,
 amino radicals substituted with one or two radicals, which may be identical or different, chosen from linear or branched $C_1$–$C_4$ alkyl radicals optionally substituted with at least one entity chosen from hydroxyl groups; amino radicals; amino radicals substituted with one or two radicals chosen from linear or branched $C_1$–$C_4$ alkyl radicals and linear or branched $C_1$–$C_4$ hydroxyalkyl radicals, which may be identical or different; ammonium groups; ($C_1$–$C_4$)alkylammonium groups, and —$SO_2NHR$ groups in which R is chosen from hydrogen and $C_1$–$C_4$ alkyl radicals, and
 —$SO_2NHR$ groups in which R is chosen from hydrogenand $C_1$–$C_4$ alkyl radicals.

In one embodiment of the present disclosure, the radicals R4, R'4, and R5 are chosen from:
 halogen atoms, for example, chlorine,
 hydroxyl groups,
 nitro groups,
 linear $C_1$–$C_2$ alkyl radicals optionally substituted with at least one hydroxyl group, and
 linear $C_1$–$C_2$ alkoxy radicals.

In another embodiment, the radicals R6, R'6, and R'7, which may be identical or different, are chosen from hydrogen and linear or branched $C_1$–$C_4$ alkyl radicals that are unsubstituted or substituted with an entity chosen from hydroxyl groups and $C_1$–$C_4$ alkoxy groups. In yet another embodiment, the radicals R6, R'6, and R'7, which may be identical or different, may be chosen from hydrogenand linear $C_1$–$C_4$ alkyl radicals.

Radicals R9 and R10, which may be identical or different, may be chosen from:
 hydrogen,
 halogen atoms, for example, chlorine and fluorine,
 nitro groups,
 cyano groups,
 hydroxyl groups,
 linear and branched $C_1$–$C_4$ alkoxy radicals,
 amino radicals,
 amino radicals substituted with one or two radicals, which may be identical or different, chosen from linear or branched $C_1$–$C_6$ alkyl radicals optionally substituted with at least one entity chosen from hydroxyl group; amino radicals; amino radicals substituted with one or two radicals chosen from linear or branched $C_1$–$C_4$ alkyl radicals and linear or branched $C_1$–$C_4$ hydroxyl radicals, which may be identical or different; ammonium groups, ($C_1$–$C_4$)alkylammonium groups, imidazolium groups, pyrazolium groups, and pyridinium groups,
 substituted amino radicals in which the radicals form an unsaturated 5- or 6-membered heterocycle optionally comprising another hetero atom chosen from oxygen and nitrogen; said heterocycle being optionally substituted.

In one embodiment of the instant disclosure, radicals R9 and R10, which may be identical or different, are chosen from:
 hydrogen,
 halogen atoms, for example, chlorine and fluorine,
 hydroxyl groups,
 amino radicals,
 amino radicals substituted with one or two identical radicals chosen from linear $C_1$–$C_4$ alkyl radicals optionally substituted with a hydroxyl group, amino radicals substituted with one or two identical linear $C_1$–$C_4$ alkyl radicals, ammonium groups, ($C_1$–$C_4$)alkylammonium groups, and imidazolium groups,
 substituted amino radicals in which the radicals form an unsaturated 5- or 6-membered heterocycle optionally comprising a nitrogen; said heterocycle being optionally substituted.

In another embodiment of the present disclosure, the radical R11 may be chosen from:
 hydrogen,
 halogen atoms, for example, chlorine ad fluorine,
 nitro groups,
 cyano groups,
 hydroxyl groups,
 linear and branched $C_1$–$C_4$ alkoxy radicals, amino radicals,
 amino radicals substituted with one or two radicals, which may be identical or different, chosen from linear or branched $C_1$–$C_6$ alkyl radicals optionally substituted with at least one entity chosen from hydroxyl groups, amino radicals, amino radicals substituted with one or two radicals chosen from linear or branched $C_1$–$C_4$ alkyl radicals and linear or branched $C_1$–$C_4$ hydroxyalkyl radicals, which may be identical or different,
 substituted amino radicals in which the radicals form an unsaturated 5- or 6-membered heterocycle optionally comprising another hetero atom chosen from oxygen and nitrogen; said heterocycle being optionally substituted.

When two radicals attached to the same nitrogen atom are linked to one another so as to form a heterocycle, the heterocycle may be chosen from pyrrolidine, piperidine, homopiperidine, piperazine, homopiperazine, and diazepane heterocycles. In addition, the heterocycle may be optionally substituted.

In one aspect of the present disclosure, the heterocycle may be chosen from pyrrolidine, 3-hydroxypyrrolidine, 3-aminopyrrolidine, 3-N,N-dimethylaminopyrrolidine, 3-trimethylammonium pyrrolidine, 3-acetamidopyrrolidine, 3-(methylsulphonylamino)-pyrrolidine, proline, 3-hydroxyproline, piperidine, hydroxypiperidine, homopiperidine, diazepane, N-methylhomopiperazine, and N-β-hydroxyethylhomopiperazine heterocycles.

In another embodiment of the present disclosure, when the coefficient r is equal to 1, the groups L1 and L3 may be chosen from:

linear or branched, substituted and unsubstituted $C_1-C_{20}$ alkylene chains optionally interrupted by at least one entity chosen from oxygen; —NR— groups, wherein R is chosen from hydrogen, linear or branched $C_1-C_4$ alkyl radicals, and linear or branched $C_1-C_4$ hydroxyalkyl radicals; —N$^+$(R')(R")— groups, wherein R' and R", which may be identical or different, are chosen from linear or branched $C_1-C_4$ alkyl radicals and linear or branched $C_1-C_4$ hydroxyalkyl radicals; carbonyl groups, and optionally substituted, cationic or noncationic, aromatic or nonaromatic heterocycles and rings; optionally terminated by a carbonyl group.

When the group L1 or L3 represents a $C_1-C_{20}$, for example, $C_1-C_8$, alkylene chain interrupted by at least one entity chosen from optionally substituted, cationic or noncationic, aromatic or nonaromatic heterocycles and rings, said heterocycle may be chosen from piperazine, homopiperazine, diazepane, pyrrolidine, (homo)piperidine, triazine, piperazinium, homopiperazinium, and imidazolium heterocycles.

In one embodiment, L1 and L3 may be chosen from substituted or unsubstituted, linear $C_1-C_8$ alkylene chains optionally interrupted by at least one entity chosen from oxygen; —NR— groups, wherein R is chosen from hydrogen, linear or branched $C_1-C_4$ alkyl radicals, and linear or branched $C_1-C_4$ hydroxyalkyl radicals; —N$^+$(R')(R")— groups, wherein R' and R", which may be identical or different, are chosen from linear or branched $C_1-C_4$ alkyl radicals and linear or branched $C_1-C_4$ hydroxyalkyl radicals; and optionally substituted heterocycles chosen from piperazine, pyrrolidine, triazine, and imidazolium heterocycles; optionally terminated by a carbonyl group.

In another embodiment of the present disclosure, L1 and L3 may be chosen from linear $C_1-C_8$ alkylene chains optionally interrupted by at least one entity chosen from oxygen; —NR— groups, wherein R is chosen from hydrogen, linear $C_1-C_4$ alkyl radicals, and —N(R')(R")$^+$— groups, wherein R' and R", which are identical, are chosen from linear $C_1-C_4$ alkyl radicals.

In at least one embodiment of the instant disclosure, the coefficient r may be equal to 0.

In another embodiment, when the coefficient s is equal to 1, the group L2 may be chosen from:

substituted or unsubstituted, linear and branched $C_1-C_{20}$ alkylene chains optionally interrupted by at least one entity chosen from oxygen; —NR— groups, wherein R is chosen from hydrogen, linear or branched $C_1-C_4$ alkyl radicals, and linear or branched $C_1-C_4$ hydroxyalkyl radicals, and —N(R')(R")$^+$— groups, wherein R' and R", which may be identical or different, are chosen from linear or branched $C_1-C_4$ alkyl radicals; linear or branched $C_1-C_4$ hydroxyalkyl radicals, optionally interrupted or terminated by at least one entity chosen from carbonyl groups and optionally substituted, cationic or noncationic, aromatic or nonaromatic heterocycles and rings;

phenylenes;

saturated or unsaturated 6- or 7-membered heterocycles comprising at least two hetero atoms, wherein the radical R6 and the nitrogen atom which carries it are part of said heterocycle.

In a further embodiment of the present disclosure, when the group L2 represents a $C_1-C_{20}$, for example, $C_1-C_8$, alkylene chain, interrupted or terminated by at least one entity chosen from aromatic or nonaromatic heterocycles and rings, said heterocycle may be chosen from piperazine, homopiperazine, diazepane, and triazine heterocycles; said heterocycles being optionally substituted.

In yet another embodiment, L2 is chosen from:

substituted and unsubstituted, linear $C_1-C_8$ alkylene chains optionally interrupted by at least one entity chosen from oxygen; —NR— groups, wherein R is chosen from hydrogen, linear or branched $C_1-C_4$ alkyl radicals, and linear or branched $C_1-C_4$ hydroxyalkyl radicals; —N(R')(R")$^+$— groups, wherein R' and R", which may be identical or different, are chosen from linear or branched $C_1-C_4$ alkyl radicals, linear or branched $C_1-C_4$ hydroxyalkyl radicals, piperazinium heterocycles, homopiperazinium heterocycles, and imidazolium heterocycles, optionally terminated by at least one carbonyl group and optionally substituted, aromatic or nonaromatic heterocycles; and phenylenes;

wherein the radical R6 and the nitrogen atom which carries it, are part of an unsubstituted piperazine or homopiperazine heterocycle.

In another embodiment, the group L2 may be chosen from:

linear $C_1-C_8$ alkylene chains optionally interrupted by at least one entity chosen from oxygen; —NR— groups, wherein R is chosen from hydrogen and linear $C_1-C_4$ alkyl radicals; and —N$^+$(R')(R")— groups, wherein R' and R", which are identical, are chosen from linear $C_1-C_4$ alkyl radicals; imidazolium heterocycles, optionally terminated by at least one entity chosen from carbonyl groups and optionally substituted, aromatic or nonaromatic heterocycles, for example, optionally substituted triazine;

phenylenes;

wherein the radical R6 and the nitrogen atom which carries it, are part of an unsubstituted piperazine or homopiperazine heterocycle.

In a further embodiment of the present disclosure, the group L2 may be a group of formula (d) below:

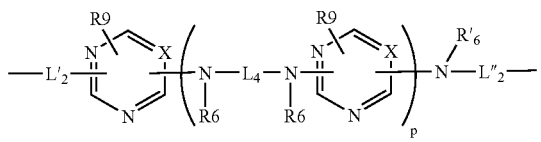

in which:

R1, R2, R3, R4, R5, R6, R'$_6$, R9 and X have the same meaning as above,

L'2 and L"2, which may be identical or different, are chosen from single bonds and $C_1-C_6$ alkylene chains, L'2 being attached to the group NR6, L4 is chosen from substituted or unsubstituted, linear or branched $C_1-C_{20}$ alkylene chains optionally interrupted by at least one entity chosen from oxygen; —NR— groups, wherein R is chosen from hydrogen, linear or branched $C_1-C_4$ alkyl radicals, and linear or branched $C_1-C_4$ hydroxyalkyl radicals; —N$^+$(R')(R")— groups, wherein R' and R", which may be identical or different, are chosen from linear or branched $C_1-C_4$ alkyl radicals and linear or branched $C_1-C_4$ hydroxyalkyl radicals, and p is a coefficient equal to 0 or 1.

Since the compounds of formula (I) and (II) and salts thereof are cationic compounds, the electroneutrality of these compounds may be satisfied by the presence of at least one cosmetically acceptable counterion An, which may be identical or different. The counterion is conventionally chosen from inorganic acid salts, for instance, chlorides, bro mides, iodides, sulphates, hydrogen sulphates, and phosphates; or from organic acid salts, such as formates, acetates, citrates, succinates, tartrates, lactates, tosylates, mesylates, benzenesulphonates, and alkyl sulphates, for instance methyl and ethyl sulphates, and mixtures thereof.

The addition salts of the compounds of formula (I) and (II), may be chosen from acid addition salts and basic addition salts. Non-limiting examples of basic addition salts include sodium hydroxide, potassium hydroxide, aqueous ammonia, amines, and alkanolamines. Examples of suitable acid addition salts include, but are not limited to inorganic acid salts, for instance, chlorides, bromides, iodides, sulphates, hydrogen sulphates, and phosphates; or from organic acid salts, such as formates, acetates, citrates, succinates, tartrates, lactates, tosylates, mesylates, benzenesulphonates, and alkyl sulphates, for instance methyl and ethyl sulphates, and mixtures thereof.

In one embodiment, the compounds of the present disclosure may correspond to formula (III) below, or salts thereof:

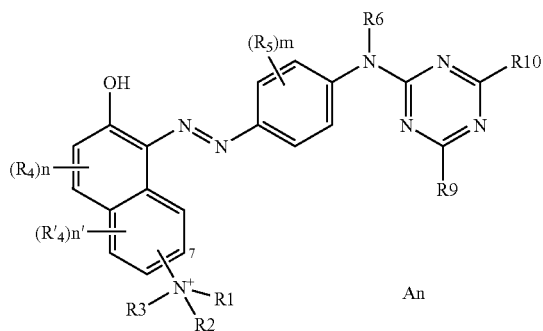

in which formula the radicals R1, R2, R3, R4, R'4, R5, R6, R9, and R10 and the coefficients n and n' have the same general and/or specific meanings indicated above.

In one embodiment of the present disclosure, in formula (III):

R1, R2 and R3, which may be identical or different, are chosen from linear or branched $C_1$–$C_4$ alkyl radicals;

R4 and R'4 represent hydrogen;

R5 is chosen from hydrogen and nitro groups;

R6 is chosen from hydrogen and linear or branched $C_1$–$C_4$ alkyl radicals, for example, methyl; and R9 and R10, which may be identical or different, are chosen from hydrogen; chlorine; fluorine; hydroxyl radicals; amino radicals; amino radicals substituted with one or two radicals chosen from linear or branched $C_1$–$C_4$ alkyl radicals and linear or branched $C_1$–$C_4$ hydroxyallyl radicals, which may be identical or different; pyrrolidine rings optionally substituted with an amino radical substituted with at least one $C_1$–$C_4$ alkyl radical, for example, methyl, which may be identical or different, optionally comprising at least one hydroxyl group; tri($C_1$–$C_4$)alkylammonium radicals with linear or branched alkyl radicals, which may be identical or different, for example, methyl;

with the proviso that R9 and R10, which may be identical or different, do not simultaneously represent a chlorine atom or a fluorine atom; and the electroneutrality of the compounds of formula (III) or of salts thereof being ensured by means of at least one cosmetically acceptable counterion An, which may be identical or different, and may be chosen from those counterions listed above.

In another embodiment, the ammonium group in formula (III) may be located in the 7-position with respect to the naphthalene ring.

Also disclosed herein are compounds corresponding to formula (IVa) below, and salts thereof:

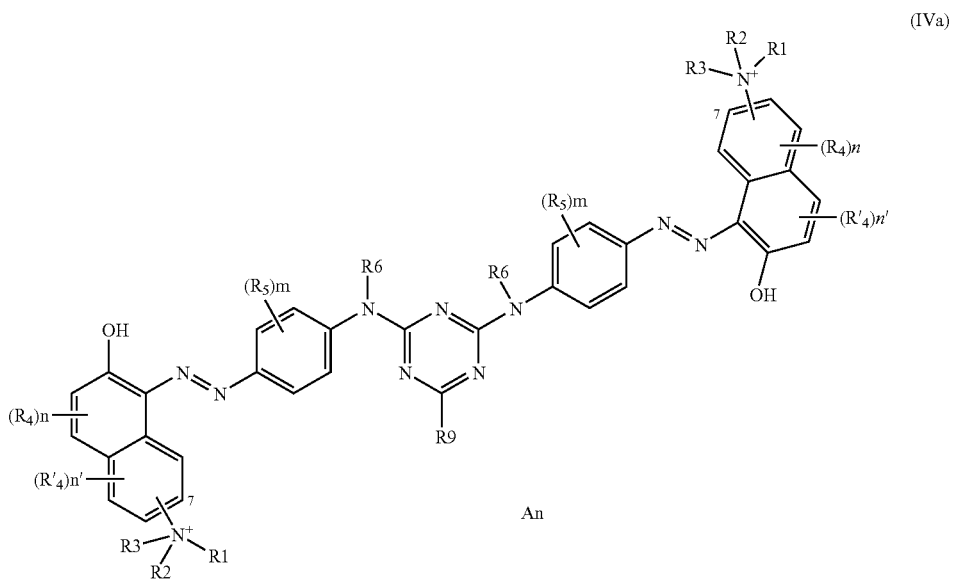

In which formula the radicals R1, R2, R3, R4, R'4, R5, R6, and R9 and the coefficients n and n' have the same general and/or specific meanings indicated above.

Further disclosed herein are compounds corresponding to formula (IVb) below:

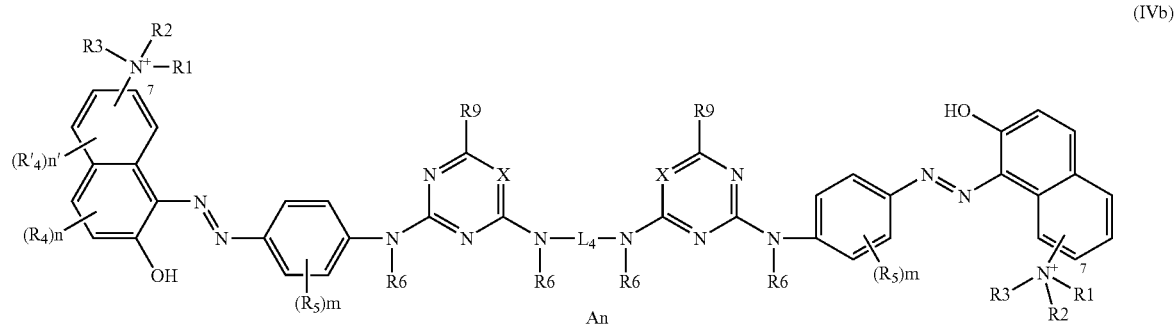

(IVb)

in which formula the radicals R1, R2, R3, R4, R'4, R5, R6, and R9 and the coefficients n and n' have the same general and/or specific meanings indicated above.

In at least one embodiment of the present disclosure, in formulae (IVa) and (IVb), the radicals:

R1, R2, and R3, which may be identical or different, are chosen from linear or branched $C_1$–$C_4$ alkyl radicals, R4 and R'4 represent hydrogen, R5 is chosen from hydrogen and nitro groups, R6 is chosen from hydrogen and linear or branched $C_1$–$C_4$ alkyl radicals, for example, methyl, and R9 is chosen from hydrogen, chlorine, fluorine, hydroxyl radicals, amino radicals, amino radicals substituted with one or two radicals chosen from linear or branched $C_1$–$C_4$ alkyl radicals and linear or branched $C_1$–$C_4$ hydroxyallyl radicals, which may be identical or different, a pyrrolidine ring optionally substituted with a trialkylammonium radical with linear or branched $C_1$–$C_4$ alkyl radicals, which may be identical or different, for example, methyl, the electroneutrality of the compounds of formula (IV) or of salts thereof being ensured by means of at least one cosmetically acceptable counterion An, which may be chosen from those counterions listed above.

In one embodiment, the ammonium group of formulae (IVa) and (IVb) may be in the 7-position with respect to the naphthalene ring.

Still further disclosed herein are compounds corresponding to formula (V) below:

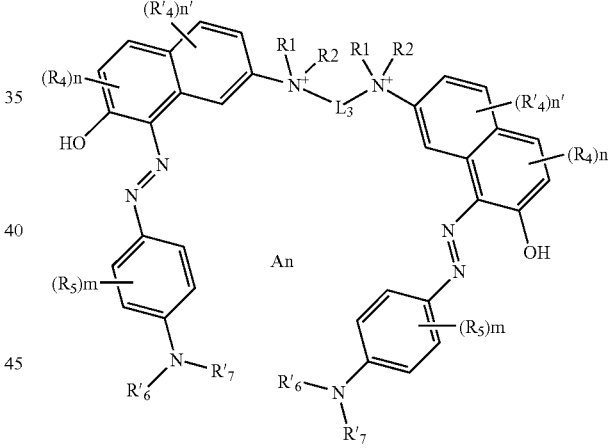

(V)

in which formula the radicals R4, R'4, R5, R'6, R'7, R1, and R2 and the coefficients n and n' have the same general and/or specific meanings indicated above.

In at least one embodiment of the present disclosure, in formula (V), the radicals R4 and R'4 represent hydrogen;

R5 is chosen from hydrogen and nitro groups;

R'6 and R'7 represent hydrogen;

R1 and R2, which may be identical or different, are chosen from linear or branched $C_1$–$C_4$ alkyl radicals and linear or branched $C_1$–$C_4$ hydroxyalkyl radicals;

L3 is chosen from linear or branched alkylene radicals comprising from 1 to 10 carbon atoms, for example, from 2 to 8 carbon atoms;

the electroneutrality of the compounds of formula (V) or of salts thereof being ensured by means of at least one cosmetically acceptable counterion An, which may be chosen from those counterions listed above.

Processes for preparing the compounds of formulae (I) and (II) and the particular variants thereof (III) to (V) will now be described.

A first process for preparing compounds of formula (I), and in particular of formula (III), comprises bringing at least one compound of formula (VI):

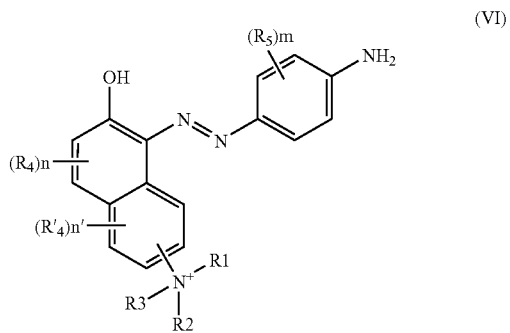

into contact with a cyanuric halide, in the presence of a solvent or of a mixture of solvents, so as to obtain a compound of formula (I) or salts thereof, in which R7 represents a group of formula (a). In general, the compound of formula (VI) is used in a solubilized form in an appropriate solvent.

In one embodiment, the solvent may be water or a mixture of water with at least one organic solvent. Suitable organic solvents may be chosen from water-soluble miscible solvents, for instance, ethanol, glycols, benzyl alcohol, acetone, and mixtures thereof.

The reaction may be carried out in the presence of at least one additive such as a pH-control agent. In one embodiment, the pH of the reaction medium may range from 3 to 6. This pH-control agent may be chosen from any art recognized pH control agent and by way of illustrative example, from aqueous ammonia, alkali metal carbonates, alkali metal hydrogen carbonates, alkanolamines such as mono-, di-, and triethanolamines, and derivatives thereof, sodium hydroxide, potassium hydroxide, and the compounds of formula (A) below:

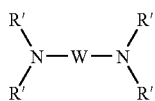

in which W is a propylene residue optionally substituted with an entity chosen from hydroxyl groups and $C_1$–$C_6$ alkyl radicals; the radicals R', which may be identical or different, are chosen from hydrogen, $C_1$–$C_6$ alkyl radicals, and $C_1$–$C_6$ hydroxyalkyl radicals. Other suitable pH-control agents include, but are not limited to, inorganic and organic acids such as hydrochloric acid, orthophosphoric acid, sulphuric acid, and acetic acid.

The pH may be maintained within a range of from 3 to 6 by the addition of a pH-control agent during the reaction.

Throughout the introduction of the compound (VI) into the compounds having a cyano function, the temperature of the reaction mixture may be maintained at a temperature below ambient temperature, for example, between 0 and 10° C. Once the introduction of the reactants is complete, the reaction mixture is maintained at a temperature greater than or equal to ambient temperature.

The reaction usually lasts from 1 to 10 hours. The product may be recovered using conventional means, for instance solvent evaporation and filtration.

To obtain compounds in which R9 does not represent a halogen atom, a substitution reaction where the halogen atom is substituted with the desired radical may be carried out in a manner that is conventional for those skilled in the art.

A second process for preparing compounds of formula (I) in which R7 represents a radical of formula (b) comprises bringing at least one compound of formula (VII)

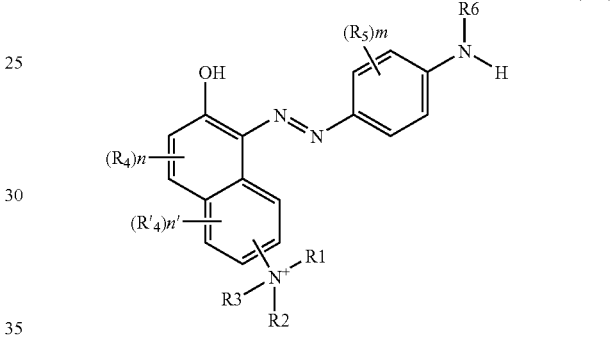

into contact with a compound that is a precursor of L2 or with a compound comprising L2 and two functions capable of reacting with the amine functions of compound (VII), in the presence of a solvent or of a mixture of solvents.

Alternatively, the process described above may be carried out so as to obtain a compound of formula (I) in which R7 represents a group of formula (a), with the appropriate amounts of compound of formula (VII) and cyanuric halide.

It is not necessary, to isolate the intermediate product obtained.

Here again, in the case of compounds in which R10 does not represent a halogen atom, a reaction consisting of substituting the halogen atom with the desired radical can be carried out in a manner that is conventional for those skilled in the art. The product can, for example, be brought into contact with an amine or water, by heating, in an appropriate solvent.

In another embodiment, a compound of formula (VIII) below:

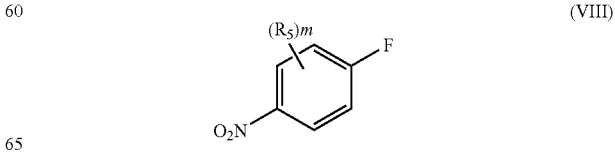

may be brought into contact with a diamine of formula $R_6NH-L_2-NHR_6$ so as to obtain a compound of formula (IX) below:

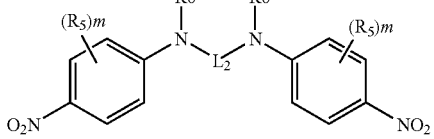

(IX)

This step may be carried out in a manner that is conventional in the field. It is generally carried out in the presence of a solvent. Suitable solvents include, for example, toluene, dichloromethane, methanol, and ethanol, and mixtures thereof. The temperature at which the reaction is carried out may conventionally range from 5 to 80° C.

Next, a step comprising the reduction of the nitro groups of the compound of formula (IX) thus obtained is carried out, followed by a diazotation step. A compound of formula (X) below is then obtained:

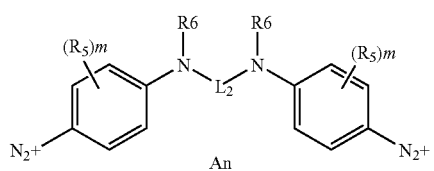

(X)

The reduction of the nitro groups may be carried out conventionally, for example, under a hydrogen pressure in the presence of a catalyst such as, for example, palladium. Conventionally, the hydrogen pressure may range from 0.01 to 10 bar. The reaction temperature may range from 5 to 80° C.

The reduction is generally carried out in an appropriate solvent. Conventionally, organic solvents may be chosen from, for example, toluene, dichloromethane, methanol, and ethanol, and mixtures thereof.

The diazotation step comprises bringing the reduced product into contact with sodium nitrite ($NaNO_2$). The temperature may range from 0 to 10° C.

At the end of this step, the product obtained is brought into contact with a compound of formula (XIa) or (XIb) below:

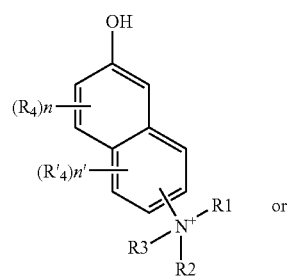

(XIa) or

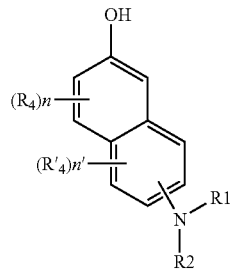

(XIb)

This step is conventionally carried out at a temperature ranging from 0 to 10° C. Moreover, the pH at which the reaction is carried out may conventionally range from 6 to 10. In one embodiment, the reaction solvent may be water.

According to one embodiment, when a compound comprising the amine function (XIb) is used, an additional, conventional step comprising quaternization of the product derived from the preceding step may be carried out.

The product may be recovered conventionally, for example, by solvent evaporation or filtration.

It is not necessary to isolate the intermediate product obtained at each step before using it in a subsequent step, unless there is incompatibility (for example, different solvents).

The compounds of formula (II) may be obtained by carrying out the following steps:

A compound of formula (XII) below:

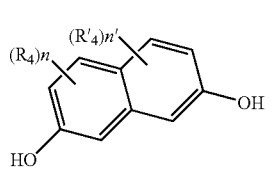

(XII)

is brought into contact with a diamine of formula $H_2N-L_3-H_2$ and a compound of formula (XIII) below is obtained:

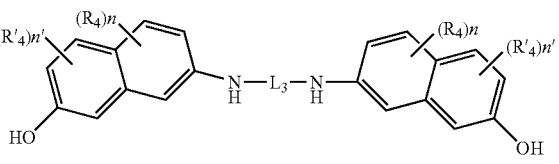

(XIII)

This reaction may be conventionally carried out in the presence of a solvent or of a mixture of solvents. Appropriate solvents may include, for example, alcohols, toluene, dichloromethane, water, and mixtures thereof.

The temperature at which this step is carried out generally ranges from 0 to 110° C.

The compound of formula (XIII) is then N-alkylated and subsequently quaternized using conventional methods.

The product thus obtained is then reacted with a compound of formula (XIV) below:

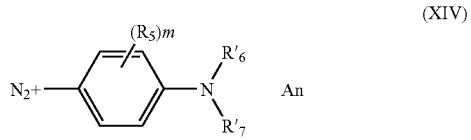

This compound may be obtained in the usual manner by diazotation of the corresponding aromatic diamine. The conditions for carrying out this step are similar to those recited in the process detailed above.

The product may be recovered conventionally, for example, by solvent evaporation or filtration.

Also disclosed herein is a dye composition comprising, in a medium suitable for dyeing keratin fibers, at least one direct dye chosen from the compounds of formulae (I) and (II) or addition salts thereof.

In one embodiment, the content of each of the compounds of formulae (I) or (II) or salts thereof may range from 0.001 to 20% by weight relative to the total weight of the dye composition. In another embodiment, the content of each of these compounds may range from 0.01 to 10% by weight relative to the total weight of the dye composition.

The dye composition according to the present disclosure may contain at least one additional direct dye that is different from the compounds of formulae (I) and (II).

As the at least one additional direct dye, direct dyes conventionally used in the field of dyeing keratin fibers, for example, human keratin fibers, may be used.

Suitable additional direct dyes may include, but are not limited to, nitro dyes of the benzene series, additional azo direct dyes, and methylene direct dyes. These direct dyes may be non-ionic, anionic, or cationic in nature. In one aspect, these additional direct dyes may be cationic in nature.

The content of each of the direct dyes may range from 0.001 to 10% by weight relative to the total weight of the dye composition.

The dye composition of the present disclosure may also contain at least one oxidation base and/or at least one coupler, conventionally used for dyeing keratin fibers such as human keratin fibers.

Non-limiting examples of oxidation bases include para-phenylenediamines, bisphenylalkylenediamines, para-aminophenols, bis-para-aminophenols, ortho-aminophenols, heterocyclic bases, and addition salts thereof.

The content of each of the oxidation bases present in the composition may range from 0.001 to 10% by weight, for example, 0.005 to 6% by weight, relative to the total weight of the dye composition.

Examples of suitable couplers include, but are not limited to, meta-phenylenediamines, meta-aminophenols, meta-diphenols, naphthalene couplers, heterocyclic couplers, and addition salts thereof.

The content of each of the couplers may range from 0.001 to 10% by weight, for example, from 0.005 to 6% by weight, relative to the total weight of the dye composition.

In general, the addition salts of the oxidation bases and of the couplers that can be used in the context of the invention may be chosen from acid addition salts, such as hydrochlorides, hydrobromides, sulphates, citrates, succinates, tartrates, lactates, tosylates, benzenesulphonates, phosphates, and acetates, and basic addition salts, such as sodium hydroxide, potassium hydroxide, aqueous ammonia, amines, and alkanolamines.

The medium suitable for dyeing, also called a dye support, may be a cosmetic medium and generally includes water or a mixture of water and at least one organic solvent in order to solubilize the compounds that are not sufficiently water-soluble.

Non-limiting examples of organic solvents include linear or branched, saturated or unsaturated monoalcohols comprising 2 to 10 carbon atoms, such as ethyl alcohol and isopropyl alcohol; aromatic alcohols, such as benzyl alcohol and phenylethyl alcohol; polyols and polyol ethers such as, for example, ethylene glycol monomethyl, monoethyl, and monobutyl ethers, propylene glycol and ethers thereof, such as, for example, propylene glycol monomethyl ether, butylene glycol, dipropylene glycol, hexylene glycol (2-methyl-2,4,-pentanediol), neopentyl glycol, and 3-methyl-1,5-pentanediol; and diethylene glycol alkyl ethers, for example, $C_1$–$C_4$ alkyl ethers, for instance diethylene glycol monoethyl ether and monobutyl ether, alone or as a mixture.

The solvents may be present in an amount ranging from 1 to 40% by weight, for example, from 5 to 30% by weight, relative to the total weight of the dye composition.

The dye composition in accordance with the present disclosure may also contain at least one adjuvant conventionally used in compositions for dyeing keratin fibers such as human keratin fibers, for example, the hair. These adjuvants may include, for example, anionic, cationic, non-ionic, amphoteric, or zwitterionic surfactants, or mixtures thereof; anionic, cationic, non-ionic, amphoteric, or zwitterionic polymers, or blends thereof; inorganic or organic thickeners, such as anionic, cationic, non-ionic, or amphoteric polymeric associative thickeners; antioxidants; penetrating agents; sequestering agents; fragrances; buffers; dispersants; conditioning agents such as, for example, volatile or non-volatile silicones, which may or may not be modified; film-forming agents; ceramides or pseudoceramides; preserving agents; opacifiers; and the like.

The adjuvants above may each be present in an amount ranging from 0.01 to 20% by weight relative to the weight of the composition.

The composition of the present disclosure may also contain at least one oxidizing agent. Oxidizing agents conventionally used for the oxidation dyeing of keratin fibers such as human keratin fibres, include, for example, hydrogen peroxide; urea peroxide; alkali metal bromates; alkali metal ferricyanides; persalts, such as perborates and persulphates of alkali metals and alkaline earth metals, for instance sodium, potassium and magnesium, alone or as mixtures; peracids; and oxidase enzymes, for example, peroxidases, 2-electron oxidoreductases such as uricases, and 4-electron oxygenases such as laccases. In at least one embodiment, the oxidizing agent is hydrogen peroxide.

The composition of the instant disclosure may also comprise at least one alkaline agent, which may be chosen from those conventionally used in the cosmetics field.

The pH of the dye composition of the invention, i.e., of the composition devoid of oxidizing agent, may range from 5 to 12, for example, from 7 to 11.

Of course, those skilled in the art will take care to choose any optional additional compound(s) in such a way that the advantageous properties intrinsically associated with the composition of the invention are not, or are not substantially, impaired by the addition envisaged.

The dye composition according to the invention may be in various forms, such as in the form of liquids, creams, or gels, or in any other forms suitable for dyeing keratin fibers such as human keratin fibres, for example, the hair.

Also disclosed herein is a method for dyeing keratin fibers comprising applying the dye composition according to the present disclosure to the fibers, which may or may not be dry.

In one embodiment of the present disclosure, the composition applied to the keratin fibers may not comprise any oxidizing agent. This embodiment may be suitable when the dye composition comprises at least one dye according to the invention and, optionally, at least one additional direct dye.

In another embodiment, the process may be carried out with at least one oxidizing agent. This embodiment may be suitable regardless of the nature of the dyes present (dye according to the invention, additional direct dye, oxidation base, and/or coupler).

The oxidizing agent may be added to the dye composition at the time of use. Alternatively it may be used from an oxidizing composition comprising it, applied simultaneously with or sequentially to the dye composition comprising the dye. In the latter case, the oxidizing agent may be present in a composition other than that comprising the dye.

In at least one embodiment, the composition comprising the dye may be mixed, for example, at the time of use, with a composition comprising, in a medium suitable for dyeing, at least one oxidizing agent, this oxidizing agent being present in an amount sufficient to obtain the desired lightening. The mixture obtained may then applied to the keratin fibers.

After an application time sufficient to obtain the desired coloration, usually ranging from 3 minutes to 1 hour, for example, from 5 to 40 minutes, the keratin fibers may be rinsed, and then optionally washed with shampoo, rinsed again, and then dried or left to dry.

Moreover, conventionally, the composition may be applied and left to act at a temperature ranging from 15 to 80° C., for example, from 15 to 40° C.

The oxidizing composition may also contain at least one adjuvant conventionally used in compositions for dyeing keratin fibers such as human keratin fibres. Non-limiting examples of suitable adjuvants are described above.

The pH of the oxidizing composition containing the oxidizing agent may be such that, after mixing with the dye composition, the pH of the resulting composition applied to the keratin fibers, i.e., the ready-to-use composition, preferably ranges from 7 to 12, for example, from 7 to 11. The pH of the ready-to-use composition may be adjusted to the desired value by means of at least one acidifying or basifying agent.

Examples of suitable acidifying agents include, but are not limited to, inorganic and organic acids, such as hydrochloric acid, orthophosphoric acid, sulphuric acid, and acetic acid.

The ready-to-use composition, i.e., the composition that is finally applied to the keratin fibers, may be in various forms, such as in the form of liquids, creams, or gels, or in any other forms suitable for dyeing keratin fibers such as human keratin fibres, for example, the hair.

Further disclosed herein is a multicompartment device in which at least a first compartment comprises a dye composition comprising at least one dye as described above, and optionally at least one direct dye different from the dye, optionally at least one oxidation base, optionally at least one coupler, and another compartment comprising an oxidizing agent.

It should be noted that the dye(s), and optionally the additional direct dye, the oxidation base(s), and the coupler(s) may be in the same compartment or in several compartments, it being possible for the same compartment to comprise a single type of dye (mixed, additional direct, or oxidation dye) or a combination of several of them.

This device may be equipped with a means for delivering the desired mixture onto the fibers to be treated, such as the devices described in French Patent No. 2 586 913.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements By way of non-limiting illustration, concrete examples of certain embodiments of the present disclosure are given below.

EXAMPLES

A—Synthesis of Dyes:

Example 1

Synthesis of compound 1: 8-{(E)-[4-({4-chloro-6-[(4-{(E)-[2-hydroxy-7-(trimethylammonio)-1-naphthyl]diazenyl}phenyl)amino]-1,3,5-triazin-2-yl}amino)-phenyl]diazenyl}-7-hydroxy-N,N,N-trimethylnaphthalen-2-aminium dichloride

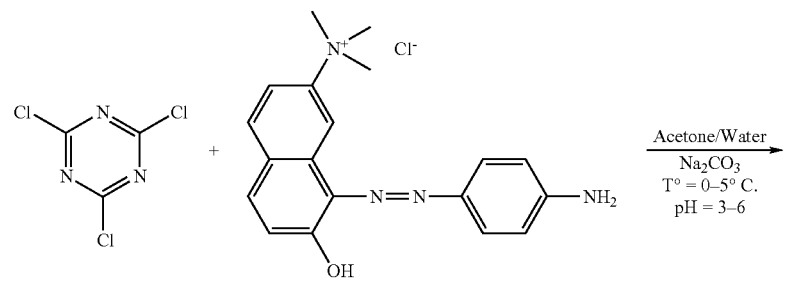

Basic Brown 16

-continued

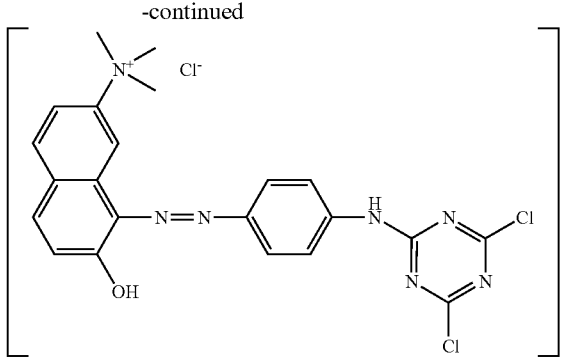

Intermediate 1

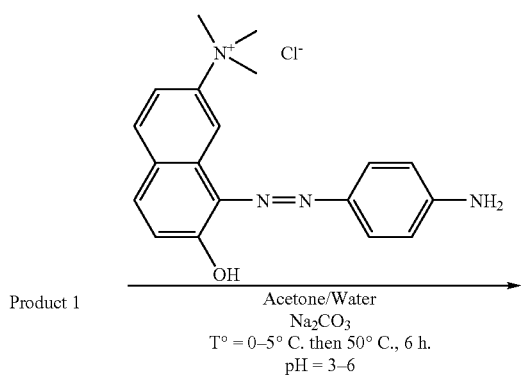

Product 1     Acetone/Water
Na$_2$CO$_3$
T° = 0–5° C. then 50° C., 6 h.
pH = 3–6

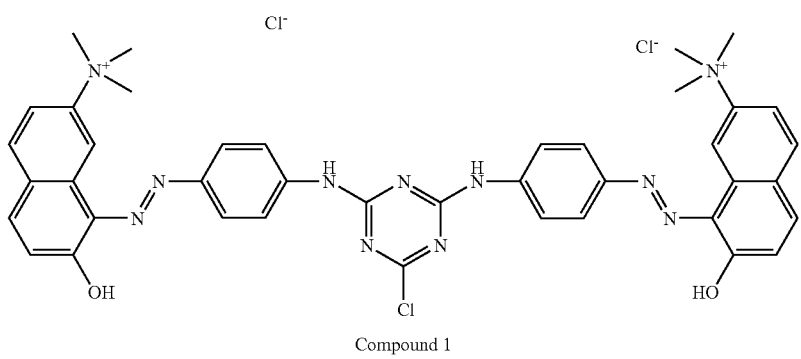

Compound 1

Basic Brown 16 dye (20 g) was dissolved in 200 ml of water. The solution obtained was then introduced slowly into a solution comprising cyanuric chloride (0.5 mol eq.), acetone (30 ml), and ice (50 g).

During the addition, the temperature was maintained at between 0 and 5° C. using a bath of water and ice. The pH was maintained at between 3 and 6 by adding solid sodium bicarbonate.

After the introduction, the reaction mixture was maintained at 40° C. for one hour, with stirring, and then at 50° C. for 6 hours.

Stabilization of the pH indicated that the reaction was complete.

The reaction mixture was then maintained at ambient temperature for 16 hours, with stirring, and a fine precipitate was obtained, which was filtered off and dried under vacuum.

Proton NMR spectrum analysis and mass spectrography confirmed that the expected product was obtained.

Examples 2 and 3

Synthesis of compound 2: 7-hydroxy-8-{(E)-[4-({4-[(2-hydroxyethyl)amino]-6-[(4-{(E)-[2-hydroxy-7-(trimethylammonio)-1-naphthyl]diazenyl}phenyl)amino]-1,3,5-triazin-2-yl}amino)phenyl]diazenyl}-N,N,N-trimethylnaphthalen-2-aminium diformate Synthesis of compound 3: 7-hydroxy-8-{(E)-[4-({4-hydroxy-6-[(4-{(E)-[2-hydroxy-7-(trimethylammonio)-1-naphthyl]diazenyl}phenyl)amino]-1,3,5-triazin-2-yl}-amino)phenyl]diazenyl}-N,N,N-trimethylnaphthalen-2-aminium diformate

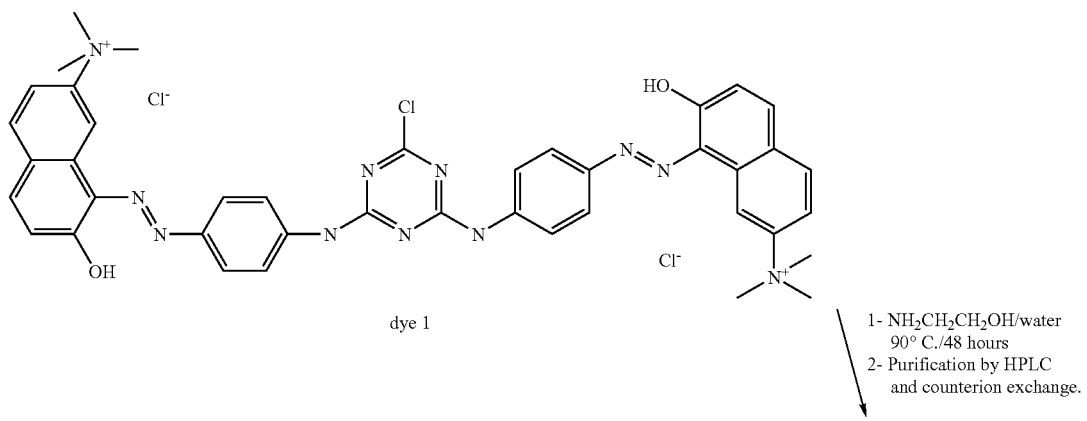

dye 1

1- $NH_2CH_2CH_2OH$/water 90° C./48 hours
2- Purification by HPLC and counterion exchange.

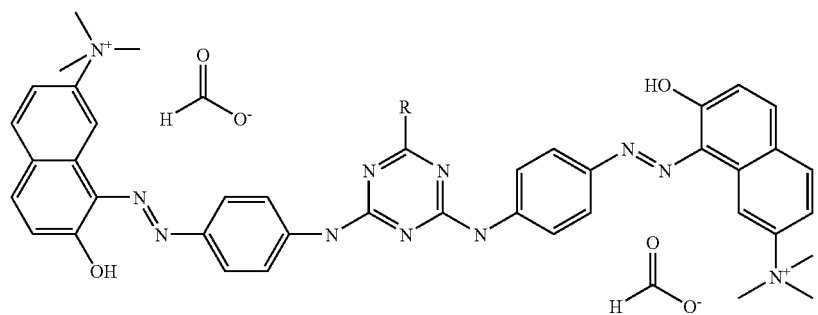

Compound 2: R = $NHCH_2CH_2OH$
Compound 3: R = OH

The compound 1 obtained above (1 g) was dissolved in 100 ml of water and monoethanolamine (1 g) was added.

After introduction, the reaction mixture was maintained at 90° C. for 48 hours, with stirring, and then evaporated to dryness.

A sample of the reaction mixture was purified by chromatography with simultaneous counterion exchange (Cl⁻ to $CH_3COO^-$) to obtain compound 2, in which R represents the group $NHCH_2CH_2OH$, and compound 3, in which R represents a hydroxyl group.

Example 4
Synthesis of compound 4: 8-((E)-{4-[(4,6-dipyrrolidin-1-yl-1,3,5-triazin-2-yl)amino]phenyl}diazenyl)-7-hydroxy-N,N,N-trimethylnaphthalen-2-aminium chloride

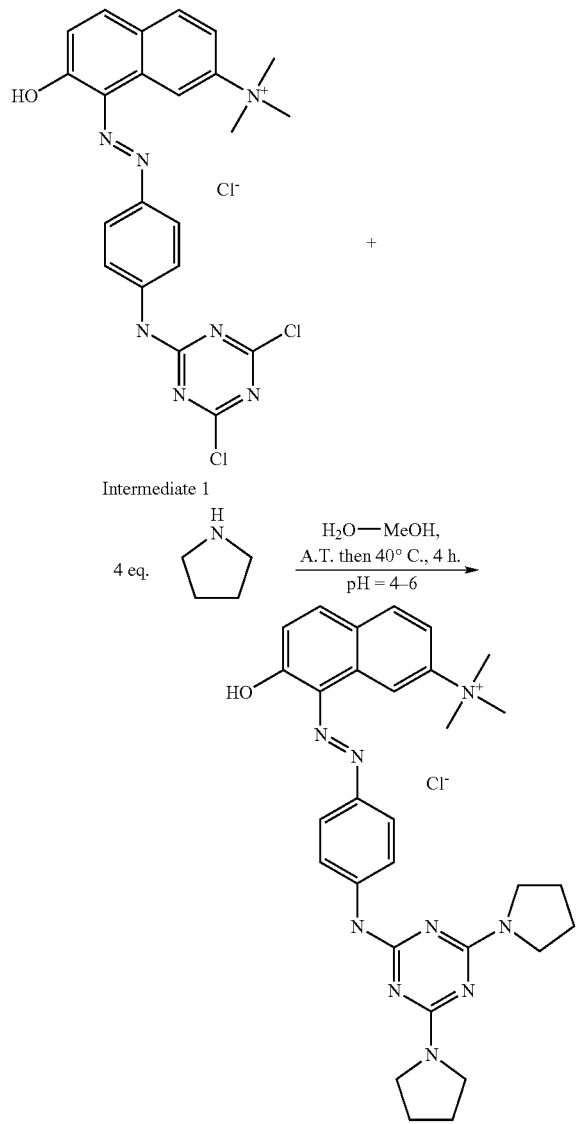

The intermediate compound 1 was obtained in the following manner:

As in the case of Example 1, Basic Brown 16 dye (20 g) was dissolved in 200 ml of water. The solution obtained was then introduced slowly into a solution comprising cyanuric chloride (0.5 mol eq), acetone (30 ml), and ice (50 g).

During the addition, the temperature was maintained at between 0 and 5° C. using a bath of water and ice. The pH was maintained at between 3 and 6 by adding solid sodium bicarbonate.

Stabilization of the pH indicated that the reaction is complete.

The product was then precipitated with acetone and then filtered and, finally, dried in a desiccator under vacuum.

Proton NMR spectrum analysis and mass spectrography confirmed that the intermediate compound I was obtained.

The intermediate compound I (1 g) was solubilized in 8 ml of a mixture comprising water and methanol (1/1).

Four equivalents of pyrrolidine were added dropwise, maintaining the pH at a value of between 4 and 6 using a 1N hydrochloric acid solution. After the addition of pyrrolidine, the reaction medium was left to stir for 12 hours and then heated for 2 hours at 40° C.

Subsequently, the reaction medium was poured into 50 ml of acetone and then filtered. The powder obtained was washed 3 times with 50 ml of acetone, and then 3 times with 50 ml of diisopropyl ether, and dried in a desiccator under vacuum.

Proton NMR spectrum analysis and mass spectrography confirmed that the expected product was obtained.

Example 5

Synthesis of compound 5: 8-{(E)-[4-({4,6-bis[3-(dimethylamino)pyrrolidin-1-yl]-1,3,5-triazin-2-yl}amino)phenyl]diazenyl}-7-hydroxy-N,N,N-trimethylnaphthalen-2-aminium chloride

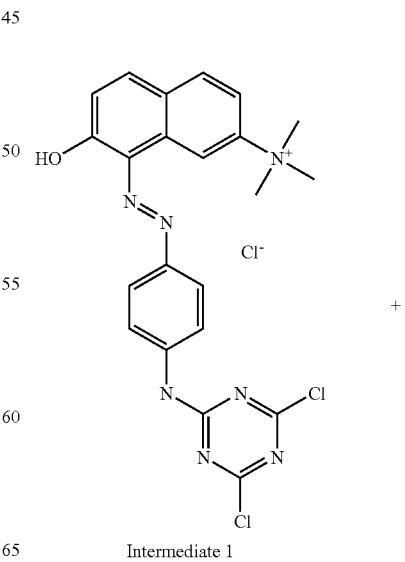

Intermediate 1

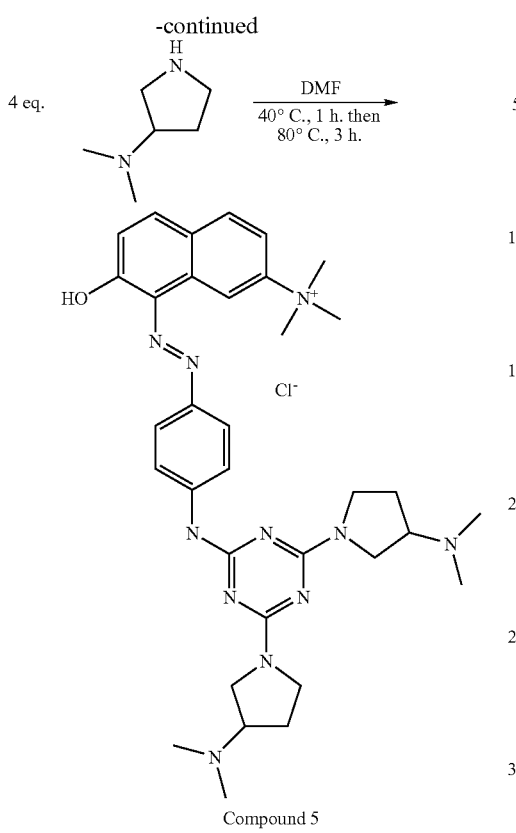

Compound 5

The intermediate compound 1 (1 g) was solubilized in 10 ml of dimethylformamide at 40° C.

Two equivalents of N,N-dimethylpyrrolidin-3-amine, diluted in 2 ml of DMF, were added and the reaction medium was maintained at 40° C. for 1 hour, and then heated at 80° C. for 2 hours.

A further 2 equivalents of N,N-dimethylpyrrolidin-3-amine, diluted in 2 ml of DMF, were added and the reaction medium was maintained at 80° C. for 1 hour.

Subsequently, the reaction mixture was poured into 50 ml of acetone and the precipitate obtained was then filtered off.

The powder obtained was washed 3 times with 50 ml of acetone, and then 3 times with 50 ml of diisopropyl ether.

The product was dried in a desiccator under vacuum.

Proton NMR spectrum analysis and mass spectrography confirmed that the expected product was obtained.

Example 6
Synthesis of compound 6: 1-{4-[(4-{(E)-[2-hydroxy-7-(trimethylammonio)-1-naphthyl]diazenyl}phenyl)amino]-6-[3-(trimethylammonio)pyrrolidin-1-yl]-1,3,5-triazin-2-yl}-N,N,N-trimethylpyrrolidin-3-aminium chloride/bis(methyl sulphate)

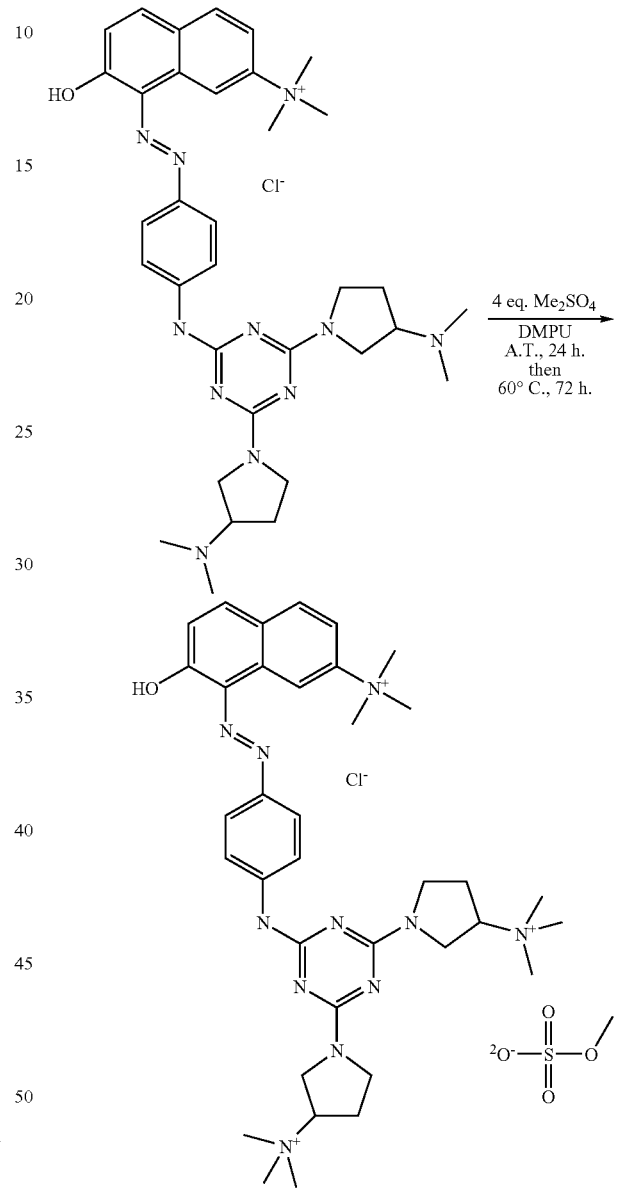

Compound 6

The compound 5 obtained in Example 5 (0.1 g) was solubilized in 2 ml of 1,3-dimethyl-3,4,5,6-tetrahydro-2(1H)-pyrimidinone (DMPU).

Two equivalents of dimethyl sulphate were added, and the reaction medium was left at ambient temperature for 24 hours, with stirring.

A further 2 equivalents of dimethyl sulphate were added, and the reaction medium was brought to 60° C. for 72 h.

Subsequently, the reaction mixture was poured into 30 ml of diisopropyl ether and then filtered. The powder obtained was washed 3 times with 50 ml of diisopropyl ether.

Proton NMR spectrum analysis and mass spectrography confirmed that the expected product was obtained.

B—Dyeing Examples

Example 7

A solution buffered at pH 9 was prepared by mixing 2 g of ammonium acetate in 30 ml of water and 10 ml of benzyl alcohol, adjusting the pH by adding aqueous ammonia, and adjusting the volume to 100 ml by adding deionized water.

Samples for each of the compounds obtained in the above examples were prepared, each sample comprising a single dye, with a concentration of $5 \times 10^{-4}$ mol per 100 g of dye in the abovementioned buffered solution.

For each sample, a lock of sensitized white hair was brought into contact with the resulting solution, with a bath ratio of 1 to 10.

After application for 30 minutes, each lock was rinsed with deionized water to remove the excess dye solution.

For each of the dyes, a brown-colored lock of hair was obtained.

Example 8

Comparative Test

Two samples were prepared, the first comprising Basic Brown 16 dye and the second comprising dye 1 obtained in Example 1, each sample comprising $5 \times 10^{-4}$ mol % of dye, in the buffered solution described in Example 7 above.

For each sample, a lock of sensitized white hair was brought into contact with the resulting solution, with a bath ratio of 1 to 10.

After application for 30 minutes, each lock was rinsed with deionized water to remove the excess dye solution.

Shampoo Test

Each lock of hair colored according to the previous step was hand-washed with a solution comprising 1% by volume of Mixa Bébé shampoo, for 30 seconds, and then rinsed with 200 ml of water. The process was repeated 10 times.

Results of the Shampoo Test

The locks obtained in the two cases kept the same color, but the intensity of the color of the lock dyed with the dye 1 in accordance with the invention was visually greater than that of the lock dyed with the Basic Brown 16.

Consequently, this shows that the dye composition according to the present invention makes it possible to obtain colorations that are more resistant to shampooing.

What is claimed is:

1. A compound of formula (I) or (II), and addition salts thereof:

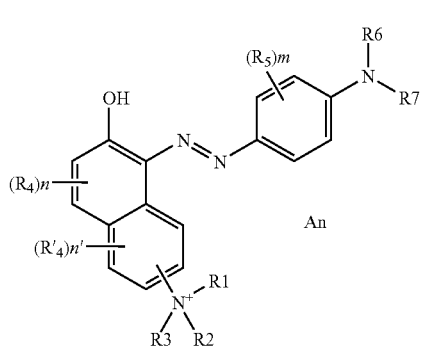

(I)

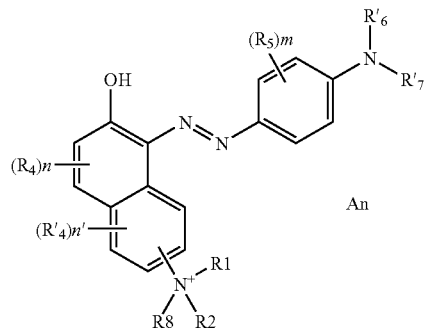

(II)

in which:

R1, R2, and R3, which may be identical or different, are chosen from:

linear or branched $C_1$–$C_4$ alkyl radicals that are unsubstituted or substituted with at least one group chosen from:

hydroxyl groups;

linear or branched $C_1$–$C_4$ alkoxy groups;

amino groups; and amino groups substituted with one or two radicals chosen from linear or branched $C_1$–$C_4$ alkyl radicals and linear or branched $C_1$–$C_4$ hydroxyalkyl radicals, which may be identical or different, wherein two of the radicals R1, R2, and R3 may optionally form a saturated or unsaturated, 5- or 6-membered heterocycle optionally comprising another hetero atom chosen from oxygen and nitrogen, said heterocycle being optionally substituted;

R4, R'4, and R5, which may be identical or different, are chosen from:

halogen atoms;

hydroxyl groups;

nitro groups cyano groups;

linear or branched $C_1$–$C_4$ alkyl radicals, optionally comprising at least one group chosen from hydroxyl groups, linear or branched $C_1$–$C_4$ alkoxy groups, amino groups and amino groups substituted with one or two radicals chosen from linear or branched $C_1$–$C_4$ alkyl radicals, which may be identical or different;

linear or branched $C_1$–$C_4$ alkoxy radicals;

amino radicals; and amino radicals substituted with one or two radicals, which may be identical or different, chosen from linear or branched $C_1$–$C_4$ alkyl radicals optionally substituted with one or two radicals chosen from:

hydroxyl groups;

amino groups;

amino groups substituted with one or two radicals chosen from linear or branched $C_1$–$C_4$ alkyl radicals and linear or branched $C_1$–$C_4$ hydroxyalkyl radicals, which may be identical or different;

substituted amino groups in which the radicals form a saturated or unsaturated 5- or 6-membered heterocycle optionally comprising another hetero atom chosen from oxygen and nitrogen; said heterocycle being optionally substituted; and —SO$_2$NHR groups in which R is chosen from hydrogen, C$_1$–C$_4$ alkyl radicals, optionally substituted with at least one radical chosen from hydroxyl radicals, amino radicals, and amino radicals substituted with one or two radicals chosen from linear or branched C$_1$–C$_4$ alkyl radicals and linear or branched C$_1$–C$_4$ hydroxyalkyl radicals, which may be identical or different, wherein two radicals R5 carried by two adjacent carbon atoms may also form, with the carbon atom to which each is attached, an optionally substituted 6-membered aromatic ring;

R6, R'6, and R'7, which may be identical or different, are chosen from:

hydrogen; and linear or branched C$_1$–C$_8$ alkyl radicals that are unsubstituted or substituted with a group chosen from hydroxyl groups, linear or branched C$_1$–C$_4$ alkoxy groups, amino groups, and amino groups substituted with one or two radicals chosen from linear or branched C$_1$–C$_4$ alkyl radicals and linear or branched C$_1$–C$_4$ hydroxyalkyl radicals, which may be identical or different; possibly interrupted with a group chosen from hetero atoms chosen from oxygen and nitrogen and groups comprising a hetero atom;

wherein the radicals R'6 and R'7 may optionally form a saturated or unsaturated 5- or 6-membered heterocycle optionally comprising another hetero atom chosen from oxygen and nitrogen; said heterocycle being optionally substituted;

R7 is chosen from groups represented by formulae (a) and (b):

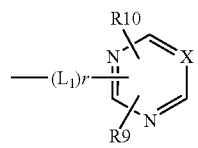

(a)

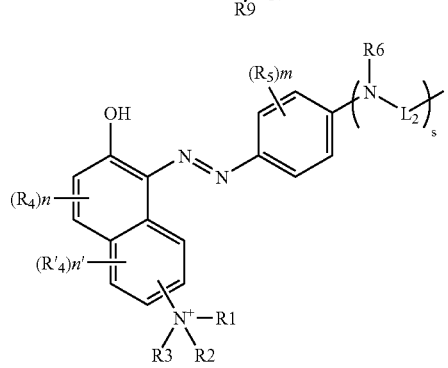

(b)

R8 is chosen from groups represented by formula (c):

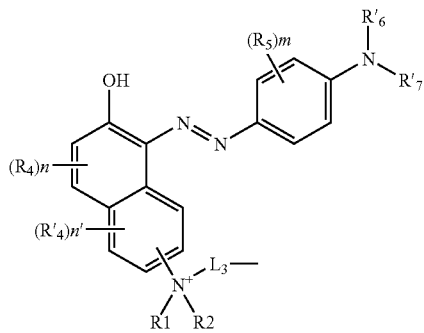

(c)

R9 and R10, which may be identical or different, are chosen from:
hydrogen,
halogen atoms,
nitro groups,
cyano groups,
linear or branched C$_1$–C$_4$ alkyl radicals optionally comprising at least one group chosen from hydroxyl groups, linear or branched C$_1$–C$_4$ alkoxy groups, amino groups, and amino groups substituted with one or two radicals chosen from linear or branched C$_1$–C$_4$ alkyl radicals, which may be identical or different,
hydroxyl groups,
linear or branched C$_1$–C$_4$ alkoxy radicals,
amino radicals,
amino radicals substituted with one or more radicals, which may be identical or different, chosen from linear or branched C$_1$–C$_6$ alkyl radicals optionally substituted with at least one radical chosen from amino, hydroxyl radicals, ammonium radicals, (C$_1$–C$_4$)alkylammonium radicals, imidazolium radicals, pyrazolium radicals, pyridinium radicals, and amino radicals substituted with at least one radical chosen from linear or branched C$_1$–C$_4$ alkyl radicals and linear or branched C$_1$–C$_4$ alkoxy radicals, which may be identical or different, and
substituted amino radicals in which the radicals form a saturated or unsaturated 5- or 6-membered heterocycle optionally comprising another hetero atom chosen from oxygen and nitrogen; said heterocycle being optionally substituted;
with the proviso that R9 and R10, which may be identical or different, may not simultaneously represent chlorine or fluorine;

X is chosen from nitrogen and the group —CR11, wherein R11 is chosen from:
hydrogen,
halogen atoms,
nitro groups,
cyano groups,
linear or branched C$_1$–C$_4$ alkyl radicals optionally comprising at least one group chosen from hydroxyl groups, linear or branched C$_1$–C$_4$ alkoxy groups, amino groups, and amino groups substituted with one or two radicals chosen from linear or branched C$_1$–C$_4$ alkyl radicals, which may be identical or different,
linear or branched C$_1$–C$_4$ alkoxy radicals,
amino radicals,
amino radicals substituted with one or two radicals, which may be identical or different, chosen from linear or branched C$_1$–C$_6$ alkyl radicals optionally substituted with at least one radical chosen from amino radicals, hydroxyl radicals, and amino radicals substituted with one or two radicals chosen from linear or branched $C_1$–$C_4$ alkyl radicals and linear or branched $C_1$–$C_4$ hydroxyalkyl radicals, which may be identical or different, and substituted amino radicals in which the radicals form a saturated or unsaturated 5- or 6-membered heterocycle optionally comprising another hetero atom chosen from oxygen or nitrogen; said heterocycle being optionally substituted;

L1, which may be cationic or noncationic, is chosen from linear, branched or cyclic, saturated or unsaturated $C_2$–$C_{20}$ hydrocarbon-based chains, optionally interrupted or terminated by a group comprising at least one hetero atom, optionally interrupted by at least one aromatic or nonaromatic, substituted or unsubstituted heterocycle or ring;

L2, which may be cationic or noncationic, is chosen from:
saturated or unsaturated, linear, branched, or cyclic $C_1$–$C_{20}$ hydrocarbon-based chains optionally interrupted or terminated by a group comprising at least one hetero atom, optionally interrupted or terminated by at least one optionally substituted, aromatic, or nonaromatic heterocycle or ring;

aromatic or nonaromatic (hetero)cyclic radicals optionally attached to the nitrogen atoms by means of a group comprising at least one hetero atom;

L3, which may be cationic or noncationic, is chosen from linear, branched, or cyclic, saturated or unsaturated $C_2$–$C_{20}$ hydrocarbon-based chains optionally interrupted or terminated by a group comprising at least one hetero atom, optionally interrupted by at least one optionally substituted aromatic or nonaromatic heterocycle or ring;

n is a coefficient being less than or equal to 2;
n' is a coefficient being less than or equal to 3;
m is a coefficient being less than or equal to 4;
r is a coefficient being equal to 0 or 1;
s is a coefficient being equal to 0 or 1; and
An is at least one cosmetically acceptable counterion for ensuring the electroneutrality of the compounds of formulae (I) and (II) or the addition salts thereof.

2. The compound of claim 1, wherein the radicals R1, R2, and R3, which may be identical or different, are chosen from linear or branched $C_1$–$C_4$ alkyl radicals that are unsubstituted or substituted with at least one group chosen from hydroxyl groups, linear or branched $C_1$–$C_4$ alkoxy radicals, amino radicals, and amino radicals, substituted with one or two radicals chosen from linear or branched $C_1$–$C_4$ alkyl radicals and linear or branched $C_1$–$C_4$ hydroxyalkyl radicals, which may be identical or different.

3. The compound of claim 2, wherein the radicals R1, R2, and R3, which may be identical or different, are chosen from linear $C_1$–$C_4$ alkyl radicals that are unsubstituted or substituted with a hydroxyl group.

4. The compound of claim 1, wherein the radicals R4, R'4, and R5 of formulae (I) and (II), which may be identical or different, are chosen from:
halogen atoms,
hydroxyl groups,
nitro groups,
linear or branched $C_1$–$C_4$ alkyl radicals optionally substituted with at least one group chosen from hydroxyl groups and linear or branched $C_1$–$C_4$ alkoxy groups,
linear or branched $C_1$–$C_4$ alkoxy radicals,
amino radicals,
amino radicals substituted with one or two radicals, which may be identical or different, chosen from linear or branched $C_1$–$C_4$ alkyl radicals optionally substituted with at least one group chosen from hydroxyl groups, amino radicals, and amino radicals substituted with one or two radicals chosen from linear or branched $C_1$–$C_4$ alkyl radicals, linear or branched $C_1$–$C_4$ hydroxyalkyl radicals, which may be identical or different, ammonium groups, ($C_1$–$C_4$)alkylammonium groups, and —$SO_2NHR$ groups in which R is chosen from hydrogen and $C_1$–$C_4$ alkyl radicals, and
—$SO_2NHR$ groups in which R is chosen from hydrogen and $C_1$–$C_4$ alkyl radicals.

5. The compound of claim 4, wherein the radicals R4, R'4, and R5 are chosen from:
halogen atoms,
hydroxyl groups,
nitro groups,
linear $C_1$–$C_2$ alkyl radicals optionally substituted with at least one hydroxyl group, and
linear $C_1$–$C_2$ alkoxy radicals.

6. The compound of claim 1, wherein the radicals R6, R'6, and R'7, which may be identical or different, are chosen from hydrogen and linear or branched $C_1$–$C_4$ alkyl radicals that are unsubstituted or substituted with a group chosen from hydroxyl groups and $C_1$–$C_4$ alkoxy groups.

7. The compound of claim 6, wherein the radicals R6, R'6, and R'7, which may be identical or different, are chosen from hydrogen and linear $C_1$–$C_4$ alkyl radicals.

8. The compound of claim 1, wherein the radicals R9 and R10, which may be identical or different, are chosen from:
hydrogen,
halogen atoms,
nitro groups,
cyano groups,
hydroxyl groups,
linear or branched $C_1$–$C_4$ alkoxy radicals,
amino radicals,
amino radicals substituted with one or two radicals, which may be identical or different, chosen from linear or branched $C_1$–$C_6$ alkyl radicals optionally substituted with at least one group chosen from hydroxyl groups, amino radicals, and amino radicals substituted with one or two radicals chosen from linear or branched $C_1$–$C_4$ alkyl radicals, linear or branched $C_1$–$C_4$ hydroxyl radicals, which may be identical or different, ammonium groups, ($C_1$–$C_4$)alkylammonium groups, imidazolium groups, pyrazolium groups, and pyridinium groups, and
substituted amino radicals in which the radicals form an unsaturated 5- or 6-membered heterocycle optionally comprising another hetero atom chosen from oxygen and nitrogen; said heterocycle being optionally substituted.

9. The compound of claim 8, wherein the radicals R9 and R10, which may be identical or different, are chosen from:
hydrogen,
halogen atoms,
hydroxyl groups,
amino radicals,
amino radicals substituted with one or two identical radicals chosen from linear $C_1$–$C_4$ alkyl radicals optionally substituted with a hydroxyl group amino radicals substituted with one or two identical linear $C_1$–$C_4$ alkyl radicals, ammonium groups, ($C_1$–$C_4$)alkylammonium groups, and imidazolium groups, and
substituted amino radicals in which the radicals form an unsaturated 5- or 6-membered heterocycle optionally comprising a nitrogen; said heterocycle being optionally substituted.

10. The compound of claim 1, wherein the radical R11 is chosen from:
halogen atoms,
nitro groups,
cyano groups, hydroxyl groups, linear or branched $C_1$–$C_4$ alkoxy radicals, amino radicals, amino radicals substituted with one or two radicals, which may be identical or different, chosen from linear or branched $C_1$–$C_6$ alkyl radicals optionally substituted with one or more hydroxyl groups, amino radicals, or amino radicals substituted with one or two linear or branched $C_1$–$C_4$ alkyl or $C_1$–$C_4$ hydroxyalkyl radicals, which may be identical or different, and substituted amino radicals in which the radicals form an unsaturated 5- or 6-membered heterocycle optionally comprising another hetero atom chosen from oxygen and nitrogen; said heterocycle being optionally substituted.

11. The compound of claim 10, wherein when the radical R11 is a substituted amino radical in which the radicals form a 5- or 6-membered heterocycle, the heterocycle is optionally substituted and chosen from pyrrolidine, piperidine, homopiperidine, piperazine, homopiperazine, and diazepane.

12. The compound of claim 11, wherein the heterocycle is chosen from pyrrolidine, 3-hydroxypyrrolidine, 3-aminopyrrolidine, 3-N,N-dimethylaminopyrrolidine, 3-trimethylammoniumpyrrolidine, 3-acetamidopyrrolidine, 3-(methylsulphonylamino)-pyrrolidine, proline, 3-hydroxyproline, piperidine, hydroxypiperidine, homopiperidine, diazepane, N-methylhomopiperazine, and N-β-hydroxyethylhomopiperazine.

13. The compound of claim 1, wherein the coefficient r is equal to 1 and the group L1 or L3 is chosen from linear or branched, substituted or unsubstituted $C_1$–$C_{20}$ alkylene chains optionally interrupted by at least one group chosen from oxygen; —NR— groups wherein R is chosen from hydrogen, linear or branched $C_1$–$C_4$ alkyl radicals, and linear or branched $C_1$–$C_4$ hydroxyalkyl radicals; —N$^+$(R') (R")— groups wherein R' and R", which may be identical or different, are chosen from linear or branched $C_1$–$C_4$ alkyl radicals and linear or branched $C_1$–$C_4$ hydroxyalkyl radicals; carbonyl groups; and optionally substituted, cationic or noncationic, aromatic or nonaromatic heterocycles or rings; optionally terminated by a carbonyl group.

14. The compound of claim 13, wherein the group L1 or L3 is chosen from $C_1$–$C_{20}$ alkylene chains interrupted by at least one optionally substituted, cationic or noncationic, aromatic or nonaromatic heterocycle or ring chosen from piperazine, homopiperazine, diazepane, pyrrolidine, (homo) piperidine, and triazine heterocycles.

15. The compound of claim 13, wherein L1 and L3 are chosen from substituted or unsubstituted, linear $C_1$–$C_8$ alkylene chains optionally interrupted by at least one group chosen from oxygen; —NR— groups, wherein R is chosen from hydrogen, linear or branched $C_1$–$C_4$ alkyl radicals, and linear or branched $C_1$–$C_4$ hydroxyalkyl radicals; —N$^+$(R') (R")— groups, wherein. R' and R", which may be identical or different, are chosen from linear or branched $C_1$–$C_4$ alkyl radicals and linear or branched $C_1$–$C_4$ hydroxyalkyl radicals; and optionally substituted heterocycles chosen from piperazine, pyrrolidine, triazine, and imidazolium; optionally terminated by a carbonyl group.

16. The compound of claim 13, wherein L1 and L3 are chosen from linear $C_1$–$C_8$ alkylene chains optionally interrupted by at least one group chosen from oxygen; —NR— groups, wherein R is chosen from hydrogen and linear $C_1$–$C_4$ alkyl radicals; and —N(R')(R")$^+$— groups, wherein R' and R", which are identical, are chosen from linear $C_1$–$C_4$ alkyl radicals.

17. The compound of claim 1, wherein the coefficient r is equal to 0.

18. The compound of claim 1, wherein the coefficient s is equal to 1 and L2 is chosen from:

substituted or unsubstituted, linear or branched $C_1$–$C_{20}$ alkylene chains optionally interrupted by at least one group chosen from oxygen; —NR— groups, wherein R is chosen from hydrogen, linear or branched $C_1$–$C_4$ alkyl radicals, and linear or branched $C_1$–$C_4$ hydroxyalkyl radicals; and —N(R')(R")$^+$— groups, wherein R' and R", which may be identical or different, are chosen from linear or branched $C_1$–$C_4$ alkyl radicals and linear or branched $C_1$–$C_4$ hydroxyalkyl radicals, optionally interrupted or terminated by at least one group chosen from carbonyl groups and optionally substituted, cationic or noncationic, aromatic or nonaromatic heterocycles or rings;

phenylenes; and saturated or unsaturated 6- or 7-membered heterocycles comprising at least two hetero atoms, the radical R6 and the nitrogen atom which carries it are part of said heterocycle.

19. The compound of claim 18, wherein L2 is chosen from $C_1$–$C_{20}$alkylene chains interrupted or terminated by at least one substituted or unsubstituted, aromatic or nonaromatic heterocycle or ring, chosen from piperazine, homopiperazine, diazepane, and triazine heterocycles.

20. The compound of claim 18, wherein L2 is chosen from:

substituted or unsubstituted, linear $C_1$–$C_8$ alkylene chains optionally interrupted by at least one group chosen from oxygen; —NR— groups, wherein R is chosen from hydrogen, linear or branched $C_1$–$C_4$ alkyl radicals, and linear or branched $C_1$–$C_4$ hydroxyalkyl radicals; —N(R')(R")$^+$— groups, wherein R' and R", which may be identical or different, are chosen from linear or branched $C_1$–$C_4$ alkyl radicals and linear or branched $C_1$–$C_4$ hydroxyalkyl radicals; piperazinium; homopiperazinium; and imidazolium, optionally terminated by at least one group chosen from carbonyl groups and optionally substituted, aromatic or nonaromatic heterocycles; and phenylenes;

wherein the radical R6 and the nitrogen atom which carries it, are part of an unsubstituted piperazine or homopiperazine heterocycle.

21. The compound of claim 18, wherein L2 represents:

linear $C_1$–$C_8$ alkylene chains optionally interrupted by at least one group chosen from oxygen; —NR— groups, wherein R is chosen from hydrogen and linear $C_1$–$C_4$ alkyl radicals; —N$^+$(R')(R")— groups, wherein R' and R", which are identical, are chosen from linear $C_1$–$C_4$ alkyl radicals; and imidazolium, optionally terminated by at least one optionally substituted, aromatic or nonaromatic heterocycle, preferably optionally substituted triazine; and phenylenes;

wherein the radical R6 and the nitrogen atom which carries it are part of an unsubstituted piperazine or homopiperazine heterocycle.

22. The compound of claim 1, wherein L2 is chosen from a group of formula (d) below:

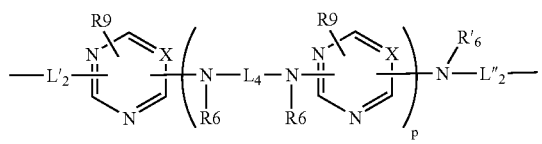

in which:

L'2 and L"2, which may be identical or different, are chosen from single bonds and $C_1$–$C_6$ alkylene chains, L'2 being attached to the group NR6, L4 is chosen from substituted or unsubstituted, linear or branched $C_1$–$C_{20}$ alkylene chains optionally interrupted by at least one group chosen from oxygen; —NR— groups, wherein R is chosen from hydrogen, linear or branched $C_1$–$C_4$ alkyl radicals, and linear or branched $C_1$–$C_4$ hydroxyalkyl radicals; —N$^+$(R')(R")— groups, wherein R' and R", which may be identical or different, are chosen from linear or branched $C_1$–$C_4$ alkyl radicals and linear or branched $C_1$–$C_4$ hydroxyalkyl radicals; and p is a coefficient equal to 0 or 1.

23. The compound of claim 1, wherein the at least one cosmetically acceptable counterion is chosen from inorganic acid salts, organic acid salts, and mixtures thereof.

24. The compound of claim 23, wherein the inorganic acid is chosen from chlorides, bromides, iodides, sulphates, hydrogen sulphates, and phosphates, and mixtures thereof.

25. The compound of claim 23; wherein the organic acid salt is chosen from formates, acetates, citrates, succinates, tartrates, lactates, tosylates, mesylates, benzenesulphonates, and alkyl sulphates, and mixtures thereof.

26. The compound of claim 1, of formula (III) below, and salts thereof:

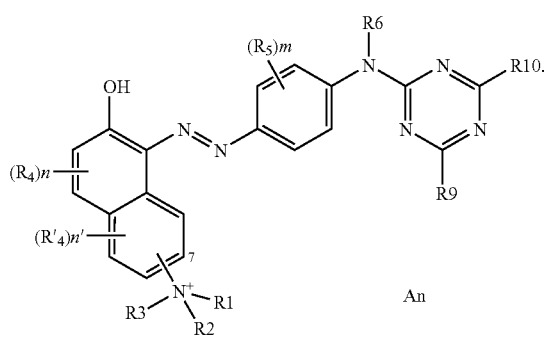

27. The compound of claim 26, wherein:

R1, R2, and R3, which may be identical or different, are chosen from linear or branched $C_1$–$C_4$ alkyl radicals;

R4 and R'4 represent hydrogen;

R5 is chosen from hydrogen and nitro groups;

R6 is chosen from hydrogen and linear or branched $C_1$–$C_4$ alkyl radicals;

R9 and R10, which may be identical or different, are chosen from hydrogen; chlorine; flourine; hydroxyl radicals; amino radicals; amino radicals substituted with one or two radicals chosen from linear or branched $C_1$–$C_4$ alkyl radicals and linear or branched $C_1$–$C_4$ hydroxyallyl radicals, which may be identical or different; and pyrrolidine rings optionally substituted with a tri($C_1$–$C_4$)alkylammonium radical with linear or branched $C_1$–$C_4$ alkyl radicals, which may be identical or different;

with the proviso that R9 and R10, which may be identical or different, may not simultaneously represent chlorine or fluorine;

the electroneutrality of the compounds of formula (III) and the salts thereof being ensured by means of at least one cosmetically acceptable counterion An, which may be identical or different, and the ammonium group being in the 7-position with respect to the naphthalene ring.

28. The compound of claim 1, of formula (IVa) or (IVb) below, and corresponding salts thereof:

(IVa):

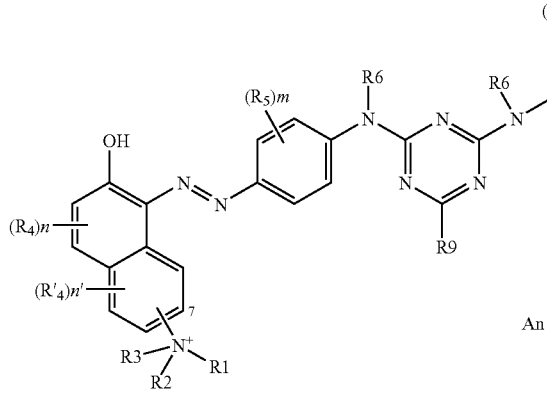

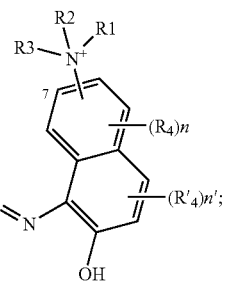

(IVb):

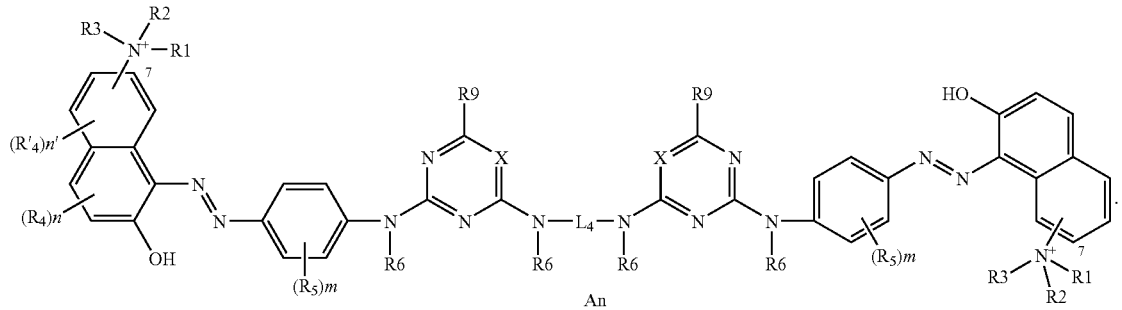

29. The compound of claim 28, wherein the radicals:
R1, R2, and R3, which may be identical or different, are chosen from linear or branched $C_1$–$C_4$ alkyl radicals,
R4 and R'4 represent hydrogen,
R5 is chosen from hydrogen and nitro groups,
R6 is chosen from hydrogen and linear or branched $C_1$–$C_4$ alkyl radicals, and
R9 is chosen from hydrogen; chlorine; fluorine; hydroxyl radicals, amino radicals, amino radicals substituted with one or two radicals chosen from linear or branched $C_1$–$C_4$ alkyl radicals and linear or branched $C_1$–$C_4$ hydroxyalkyl radicals, which may be identical or different; and pyrrolidine rings optionally substituted with a tri($C_1$–$C_4$)alkylammonium radical with linear or branched $C_1$–$C_4$ alkyl radicals, which may be identical or different, the electroneutrality of the compounds of formula (IV) and the salts thereof being ensured by means of at least one cosmetically acceptable counterion An, which may be identical or different,
the ammonium group of formulae (IVa) and (IVb) being in the 7-position with respect to the diaromatic ring.

30. The compound of claim 1, of formula (V) below:

(V)

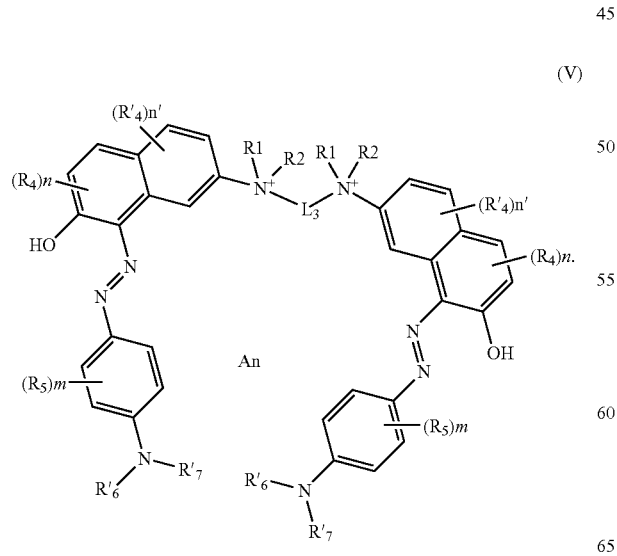

31. The compound of claim 30, wherein the radicals:
R4 and R'4 represent hydrogen;
R5 is chosen from hydrogen and nitro groups;
R'6 and R'7 represent hydrogen;
R12 and R13, which may be identical or different, are chosen from hydrogen, linear or branched $C_1$–$C_4$ alkyl radicals and linear or branched $C_1$–$C_4$ hydroxyalkyl radicals; and
L3 is chosen from linear or branched alkylene radicals comprising from 1 to 10 carbon atoms;
the electroneutrality of the compounds of formula (V) and the salts thereof being ensured by means of at least one cosmetically acceptable counterion An, which may be identical or different.

32. A process for preparing the compound of claim 1, comprising contacting a compound of formula (VI):

(VI)

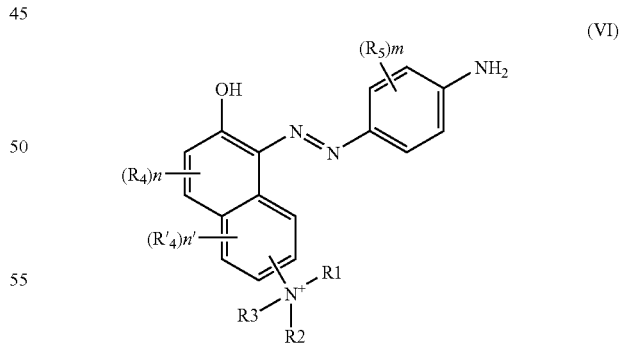

with a cyanuric halide, in the presence of a solvent or of a mixture of solvents, so as to obtain a compound of formula (I), in which R7 represents a group of formula (a).

33. A process for preparing the compound of claim 1, comprising contacting a compound of formula (VII)

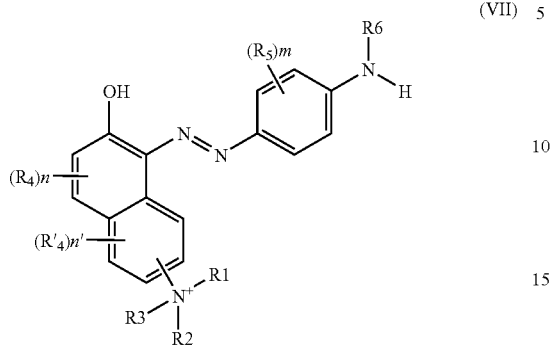

with a compound that is a precursor of L2 or with a compound comprising L2 and two functions capable of reacting with the amine functions of compound (VI), in the presence of a solvent or of a mixture of solvents, so as to obtain a compound of formula (I) in which R7 represents a group of formula (b).

34. The process of claim 33, wherein the compound of formula (VI) and cyanuric halide are brought into contact.

35. A process for preparing the compound of claim 1, comprising:
(a) contacting a compound of formula (VIII) below:

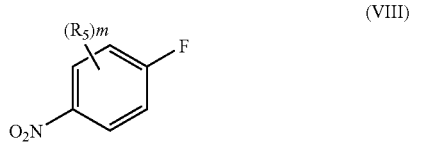

with a diamine of formula $R_6NH-L_2-NHR_6$ so as to obtain a compound of formula (IX) below:

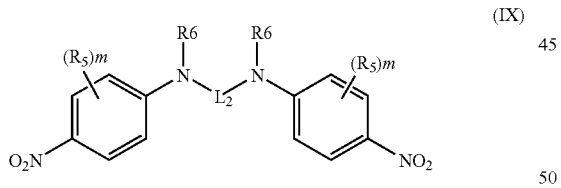

(b) reducing the nitro groups of the compound out of formula (IX), in the presence of hydrogen and a catalyst,
(c) performing a diazotation of the reduced compound so as to obtain the compound of formula (X) below:

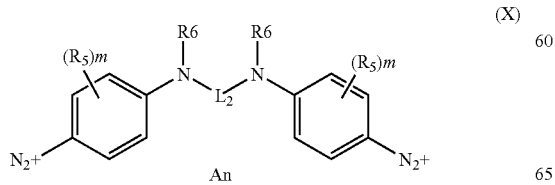

(d) contacting the product (X) with a compound of formula (XIa) or (XIb) below:

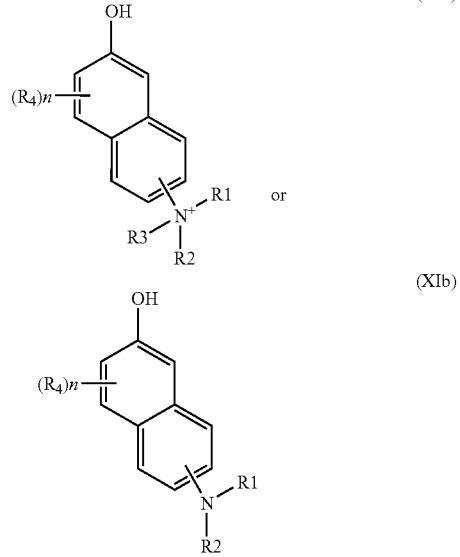

(XIa)

wherein when the compound comprising the amine function is used, an additional step consisting of quaternization of the resultant product is carried out.

36. A process for preparing the compound of claim 1, comprising:
(a) contacting a compound of formula (XII) below:

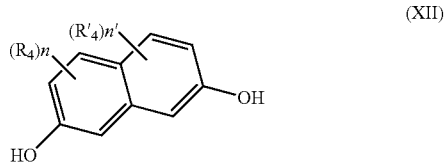

with a diamine of formula $H_2N-L_3-NH_2$ so as to obtain a compound of formula (XIII) below:

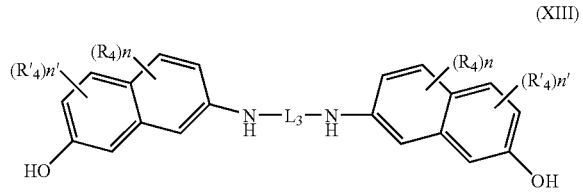

(b) carrying out an N-alkylation, followed by quaternization of the product (XIII),
(c) reacting the resulting product with a compound of formula (XIV) below:

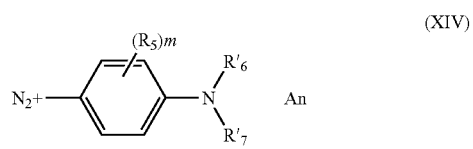

to obtain a compound of formula (II).

37. A dye composition comprising, in a medium suitable for dyeing keratin fibers, at least one compound of claim 1, as direct dye.

38. The composition of claim 37, wherein the content of each of the compounds of formulae (I) and (II), and salts thereof, ranges from 0.001 to 20% by weight relative to the total weight of the dye composition.

39. A method for dyeing keratin fibers, in which the dye composition of claim 37 is applied to dry or wet fibers, without final rinsing.

40. A method for dyeing keratin fibers, in which the dye composition of claim 37 is applied to dry or wet fibers for a period of time sufficient to develop the coloration, after which the fibres are rinsed and/or washed with shampoo.

* * * * *

UNITED STATES PATENT AND TRADEMARK OFFICE
CERTIFICATE OF CORRECTION

| | |
|---|---|
| PATENT NO. | : 7,235,645 B2 |
| APPLICATION NO. | : 11/187812 |
| DATED | : June 26, 2007 |
| INVENTOR(S) | : Andrew Greaves et al. |

It is certified that error appears in the above-identified patent and that said Letters Patent is hereby corrected as shown below:

On the Title Page, after Item (60), "Related U.S. Application Data", and before Item (51), "Int. Cl.", insert the following missing data:
--(30)  Foreign Application Priority Data
 Jul. 23, 2004 (FR)     04 08186--.

Column 32, line 43, "nitro groups" should read --nitro groups;--.

Column 35, line 47, "amino radicals, substituted" should read --amino radicals substituted--.

Column 36, lines 56-57, "hydroxyl group amino radicals" should read --hydroxyl group, amino radicals--.

Column 37, line 52, "wherein. R' and R"," should read --wherein R' and R",--.

Column 38, line 19, "$C_1$-$C_{20}$alkylene" should read --$C_1$-$C_{20}$ alkylene--.

Column 39, line 18, "claim 23; wherein" should read --claim 23, wherein--.

Column 40, line 12, "flourine;" should read --fluorine;--.

Column 40, line 17, "hydroxyallyl" should read --hydroxyalkyl--.

Column 44, line 25, delete "(XIa)".

Column 44, line 27, "function is" should read --function (XIb) is--.

UNITED STATES PATENT AND TRADEMARK OFFICE
CERTIFICATE OF CORRECTION

PATENT NO.       : 7,235,645 B2
APPLICATION NO.  : 11/187812
DATED            : June 26, 2007
INVENTOR(S)      : Andrew Greaves et al.

It is certified that error appears in the above-identified patent and that said Letters Patent is hereby corrected as shown below:

Column 44, lines 45-51, in the structure for formula (XIII),

"
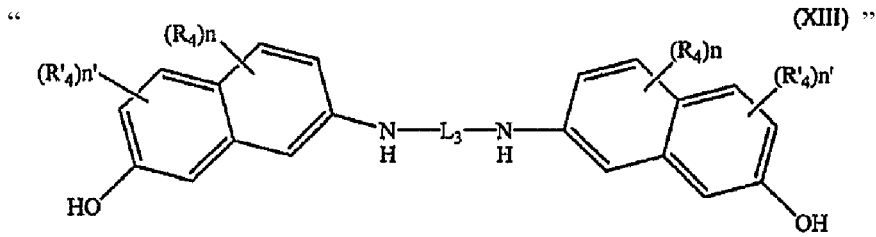
(XIII) "

should read

--
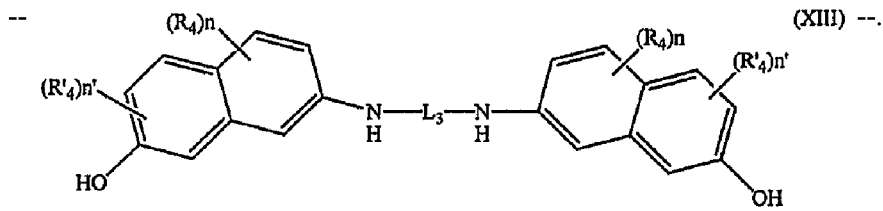
(XIII) --.

Signed and Sealed this

Twenty-seventh Day of November, 2007

JON W. DUDAS
*Director of the United States Patent and Trademark Office*